United States Patent
Ziniti et al.

(12) 
(10) Patent No.: US 9,750,492 B2
(45) Date of Patent: Sep. 5, 2017

(54) SUTURE ANCHOR SYSTEM WITH TENSION RELIEF MECHANISM

(75) Inventors: Donald Ziniti, Cumberland, RI (US); Kevin J. Ranucci, Warwick, RI (US); Armand A. Morin, Berkley, MA (US)

(73) Assignee: DEPUY MITEK, LLC, Raynham, MA (US)

(*) Notice: Subject to any disclaimer, the term of this patent is extended or adjusted under 35 U.S.C. 154(b) by 1478 days.

(21) Appl. No.: 11/462,416

(22) Filed: Aug. 4, 2006

(65) Prior Publication Data

US 2008/0033460 A1   Feb. 7, 2008

(51) Int. Cl.
*A61B 17/04* (2006.01)

(52) U.S. Cl.
CPC ...... *A61B 17/0401* (2013.01); *A61B 17/0483* (2013.01); *A61B 17/0487* (2013.01); *A61B 2017/045* (2013.01); *A61B 2017/0409* (2013.01); *A61B 2017/0414* (2013.01); *A61B 2017/0445* (2013.01); *A61B 2017/0464* (2013.01); *A61B 2017/0496* (2013.01)

(58) Field of Classification Search
CPC ........ A61B 2017/0454; A61B 17/0487; A61B 2017/0414; A61B 2017/0412; A61B 2017/045; A61B 2017/06176; A61B 2017/0445; A61B 2017/0446; A61B 2017/0496; A61B 2017/0409
USPC .................................................. 606/232, 148
See application file for complete search history.

(56) References Cited

U.S. PATENT DOCUMENTS

| | | |
|---|---|---|
| 2,381,050 A | 8/1945 | Hardinge |
| 3,035,583 A | 5/1962 | Hirsch |
| 3,036,482 A | 5/1962 | Kenworthy |
| 3,103,926 A | 9/1963 | Cochran |
| 3,135,414 A | 6/1964 | Lee, II |
| 3,525,365 A | 8/1970 | Meulendyk |
| 3,566,739 A | 3/1971 | Lebar |
| 3,708,883 A | 1/1973 | Flander |
| 3,760,802 A | 9/1973 | Fischer |
| 3,842,824 A | 10/1974 | Neufeld |
| 4,013,071 A | 3/1977 | Rosenberg |
| 4,091,806 A | 5/1978 | Aginsky |
| 4,112,814 A | 9/1978 | Schafers |
| 4,140,111 A | 2/1979 | Morrill |
| 4,408,938 A | 10/1983 | Maguire |
| 4,447,915 A | 5/1984 | Weber |

(Continued)

FOREIGN PATENT DOCUMENTS

| | | |
|---|---|---|
| CA | 2153594 | 7/1994 |
| CA | 2303853 | 4/1999 |

(Continued)

OTHER PUBLICATIONS

Co-pending U.S. Appl. No. 11/462,419, filed Aug. 4, 2006.

(Continued)

*Primary Examiner* — Jing Ou

(57) ABSTRACT

Methods and devices are provided for attaching soft tissue to bone. In general, a deployment device, insertion assembly, and suture anchor are provided. The insertion assembly is coupled between the deployment device and the suture anchor to allow the deployment device to deploy the suture anchor into bone. Each of the various components disclosed herein can be used alone, in combination with one another, or in combination with various other devices.

22 Claims, 16 Drawing Sheets

(56) References Cited

U.S. PATENT DOCUMENTS

| | | |
|---|---|---|
| 4,475,856 A | 10/1984 | Toomingas |
| 4,484,570 A | 11/1984 | Sutter |
| 4,492,226 A | 1/1985 | Belykh |
| 4,498,468 A | 2/1985 | Hansson |
| 4,506,670 A | 3/1985 | Crossley |
| 4,590,928 A | 5/1986 | Hunt |
| 4,632,100 A | 12/1986 | Somers |
| 4,708,132 A | 11/1987 | Silvestrini |
| 4,711,232 A | 12/1987 | Fischer |
| 4,716,893 A | 1/1988 | Fischer |
| 4,738,255 A | 4/1988 | Goble et al. |
| 4,741,330 A | 5/1988 | Hayhurst |
| 4,760,843 A | 8/1988 | Fischer et al. |
| 4,778,468 A | 10/1988 | Hunt |
| 4,790,304 A | 12/1988 | Rosenberg |
| 4,797,044 A | 1/1989 | Velasco |
| 4,834,752 A | 5/1989 | Van Kampen |
| 4,870,957 A | 10/1989 | Goble |
| 4,871,289 A | 10/1989 | Choiniere |
| 4,873,976 A | 10/1989 | Schreiber |
| 4,924,865 A | 5/1990 | Bays |
| 4,927,421 A | 5/1990 | Goble |
| 4,940,467 A | 7/1990 | Tronzo |
| 4,944,742 A | 7/1990 | Clemow |
| 4,988,351 A | 1/1991 | Paulos |
| 5,013,316 A | 5/1991 | Goble |
| 5,037,422 A | 8/1991 | Hayhurst |
| 5,046,513 A | 9/1991 | Gatturna |
| 5,059,206 A | 10/1991 | Winters |
| 5,078,718 A | 1/1992 | Moll |
| 5,084,050 A | 1/1992 | Draenert |
| 5,116,337 A | 5/1992 | Johnson |
| 5,122,132 A | 6/1992 | Bremer |
| 5,141,373 A | 8/1992 | Kendall |
| 5,141,520 A | 8/1992 | Goble |
| 5,152,735 A | 10/1992 | Podd, Jr. |
| 5,152,763 A | 10/1992 | Johnson |
| 5,154,189 A | 10/1992 | Oberlander |
| 5,169,400 A | 12/1992 | Muhling |
| 5,176,682 A | 1/1993 | Chow |
| 5,203,784 A | 4/1993 | Ross |
| 5,207,579 A | 5/1993 | Campagnuolo |
| 5,207,679 A | 5/1993 | Li |
| 5,209,753 A | 5/1993 | Biedermann |
| RE34,293 E | 6/1993 | Goble |
| 5,224,946 A | 7/1993 | Hayhurst |
| 5,236,445 A | 8/1993 | Hayhurst |
| 5,244,946 A | 9/1993 | Guest |
| 5,248,231 A | 9/1993 | Denham |
| 5,257,637 A | 11/1993 | El Gazayerli |
| 5,258,015 A | 11/1993 | Li |
| 5,261,914 A | 11/1993 | Warren |
| 5,268,001 A | 12/1993 | Nicholson |
| 5,269,783 A | 12/1993 | Sander |
| 5,314,427 A | 5/1994 | Goble |
| 5,324,308 A | 6/1994 | Pierce |
| 5,326,205 A | 7/1994 | Anspach, Jr. |
| 5,352,229 A | 10/1994 | Goble |
| 5,354,298 A | 10/1994 | Lee |
| 5,370,662 A | 12/1994 | Stone |
| 5,380,334 A | 1/1995 | Torrie |
| 5,400,805 A | 3/1995 | Warren |
| 5,411,523 A | 5/1995 | Goble |
| 5,417,712 A | 5/1995 | Whittaker |
| 5,423,860 A | 6/1995 | Lizardi |
| 5,441,502 A | 8/1995 | Bartlett |
| 5,458,601 A | 10/1995 | Young, Jr. |
| 5,464,427 A | 11/1995 | Curtis |
| 5,466,243 A | 11/1995 | Schmieding |
| 5,472,452 A | 12/1995 | Trott |
| 5,480,403 A * | 1/1996 | Lee et al. ............. 606/232 |
| 5,486,197 A | 1/1996 | Le |
| 5,489,210 A | 2/1996 | Hanosh |
| 5,496,326 A | 3/1996 | Johnson |
| 5,501,683 A | 3/1996 | Trott |
| 5,501,695 A | 3/1996 | Anspach, Jr. |
| 5,520,700 A | 5/1996 | Beyar |
| 5,522,817 A | 6/1996 | Sander |
| 5,522,844 A | 6/1996 | Johnson |
| 5,522,845 A | 6/1996 | Wenstrom, Jr. |
| 5,531,792 A | 7/1996 | Huene |
| 5,534,012 A | 7/1996 | Bonutti |
| 5,545,180 A | 8/1996 | Le |
| 5,569,306 A | 10/1996 | Thal |
| 5,571,104 A | 11/1996 | Li |
| 5,584,835 A | 12/1996 | Greenfield |
| 5,591,207 A | 1/1997 | Coleman |
| 5,601,558 A | 2/1997 | Torrie |
| 5,626,614 A | 5/1997 | Hart |
| 5,643,320 A | 7/1997 | Lower |
| 5,643,321 A | 7/1997 | McDevitt |
| 5,649,963 A | 7/1997 | McDevitt |
| 5,658,313 A | 8/1997 | Thal |
| 5,665,112 A | 9/1997 | Thal |
| 5,683,419 A | 11/1997 | Thal |
| 5,690,676 A | 11/1997 | DiPoto |
| 5,702,397 A | 12/1997 | Goble |
| 5,702,462 A | 12/1997 | Oberlander |
| 5,707,395 A | 1/1998 | Li |
| 5,709,708 A | 1/1998 | Thal |
| 5,713,903 A | 2/1998 | Sander |
| 5,720,753 A | 2/1998 | Sander |
| 5,720,765 A | 2/1998 | Thal |
| 5,725,529 A | 3/1998 | Nicholson et al. |
| 5,725,541 A | 3/1998 | Anspach, III |
| 5,728,136 A | 3/1998 | Thal |
| 5,759,184 A | 6/1998 | Santangelo |
| 5,759,313 A | 6/1998 | Shirai |
| 5,782,865 A | 7/1998 | Grotz |
| 5,791,899 A | 8/1998 | Sachdeva |
| 5,797,963 A | 8/1998 | McDevitt |
| 5,800,436 A | 9/1998 | Lerch |
| 5,814,071 A | 9/1998 | McDevitt |
| 5,814,072 A | 9/1998 | Bonutti |
| 5,814,073 A | 9/1998 | Bonutti |
| 5,845,645 A | 12/1998 | Bonutti |
| 5,849,004 A | 12/1998 | Bramlet |
| 5,860,978 A | 1/1999 | McDevitt |
| 5,902,321 A | 5/1999 | Caspari |
| 5,911,721 A * | 6/1999 | Nicholson et al. ............. 606/326 |
| 5,928,244 A | 7/1999 | Tovey |
| RE36,289 E | 8/1999 | Le |
| 5,935,129 A | 8/1999 | McDevitt |
| 5,935,134 A | 8/1999 | Pedlick |
| 5,948,000 A | 9/1999 | Larsen et al. |
| 5,948,002 A | 9/1999 | Bonutti |
| 5,957,924 A | 9/1999 | Tormala |
| 5,957,953 A | 9/1999 | DiPoto et al. |
| 5,968,044 A | 10/1999 | Nicholson |
| 5,968,078 A | 10/1999 | Grotz |
| 5,980,558 A | 11/1999 | Wiley |
| 5,980,559 A | 11/1999 | Bonutti |
| 5,993,459 A | 11/1999 | Larsen |
| 6,022,352 A | 2/2000 | Vandewalle |
| 6,039,740 A | 3/2000 | Olerud |
| 6,042,584 A | 3/2000 | Pierson, III |
| 6,051,791 A | 4/2000 | King |
| 6,056,751 A | 5/2000 | Fenton, Jr. |
| 6,056,772 A | 5/2000 | Bonutti |
| 6,086,608 A | 7/2000 | Ek |
| 6,099,530 A | 8/2000 | Simonian |
| 6,099,547 A | 8/2000 | Gellman |
| 6,117,160 A | 9/2000 | Bonutti |
| 6,117,161 A | 9/2000 | Li |
| 6,123,711 A | 9/2000 | Winters |
| 6,126,662 A | 10/2000 | Carmichael |
| 6,139,565 A | 10/2000 | Stone |
| RE36,974 E | 11/2000 | Bonutti |
| 6,143,017 A | 11/2000 | Thal |
| 6,146,406 A | 11/2000 | Shluzas |
| 6,146,408 A | 11/2000 | Bartlett |
| 6,149,669 A | 11/2000 | Li |
| 6,159,234 A | 12/2000 | Bonutti |
| 6,162,234 A | 12/2000 | Freedland |

(56) References Cited

U.S. PATENT DOCUMENTS

| | | |
|---|---|---|
| 6,162,236 A | 12/2000 | Osada |
| 6,165,203 A | 12/2000 | Krebs |
| 6,168,598 B1 | 1/2001 | Martello |
| 6,174,324 B1 | 1/2001 | Egan |
| 6,200,329 B1 | 3/2001 | Fung |
| 6,203,572 B1 | 3/2001 | Johnson |
| 6,227,860 B1 | 5/2001 | Hobo |
| 6,228,096 B1 | 5/2001 | Marchand |
| 6,241,732 B1 | 6/2001 | Overaker et al. |
| 6,248,108 B1 | 6/2001 | Törmälä |
| 6,267,766 B1 | 7/2001 | Burkhart |
| 6,280,191 B1 | 8/2001 | Gordon |
| 6,290,701 B1 | 9/2001 | Enayati |
| 6,302,886 B1 | 10/2001 | McDevitt |
| 6,309,405 B1 | 10/2001 | Bonutti |
| 6,319,252 B1 | 11/2001 | McDevitt |
| 6,319,269 B1 | 11/2001 | Li |
| 6,332,778 B1 | 12/2001 | Choung |
| 6,368,326 B1 | 4/2002 | Dakin |
| 6,391,030 B1 | 5/2002 | Wagner et al. |
| 6,413,260 B1 | 7/2002 | Berrevoets |
| 6,423,062 B2 | 7/2002 | Enayati |
| 6,447,516 B1 | 9/2002 | Bonutti |
| 6,497,707 B1 | 12/2002 | Bowman et al. |
| 6,517,543 B1 | 2/2003 | Berrevoets |
| 6,517,578 B2 | 2/2003 | Hein |
| 6,517,579 B1 | 2/2003 | Paulos |
| 6,520,980 B1 | 2/2003 | Foerster |
| 6,524,316 B1 | 2/2003 | Nicholson |
| 6,527,794 B1 | 3/2003 | McDevitt |
| 6,547,792 B1 | 4/2003 | Tsuji |
| 6,641,596 B1 | 11/2003 | Lizardi |
| 6,660,023 B2 | 12/2003 | McDevitt |
| 6,673,094 B1 | 1/2004 | McDevitt |
| 6,689,135 B2 | 2/2004 | Enayati |
| 6,689,140 B2 | 2/2004 | Cohen |
| 6,733,506 B1 | 5/2004 | McDevitt |
| 6,770,073 B2 | 8/2004 | McDevitt |
| 6,778,861 B1 | 8/2004 | Liebrecht |
| 6,780,198 B1* | 8/2004 | Gregoire et al. ............ 606/232 |
| 6,840,953 B2 | 1/2005 | Martinek |
| 6,932,834 B2 | 8/2005 | Lizardi |
| 7,074,203 B1 | 7/2006 | Johanson |
| 7,081,126 B2 | 7/2006 | McDevitt |
| 7,329,271 B2 | 2/2008 | Koyfman et al. |
| 7,357,810 B2 | 4/2008 | Koyfman et al. |
| 7,381,213 B2 | 6/2008 | Lizardi |
| 8,491,600 B2 | 7/2013 | McDevitt et al. |
| 8,518,091 B2 | 8/2013 | McDevitt et al. |
| 2001/0005475 A1 | 6/2001 | Frigg |
| 2001/0053913 A1 | 12/2001 | Freedland |
| 2002/0040241 A1 | 4/2002 | Jarvinen |
| 2002/0115999 A1 | 8/2002 | McDevitt et al. |
| 2002/0147463 A1 | 10/2002 | Martinek |
| 2003/0004545 A1 | 1/2003 | Burkhart |
| 2003/0130695 A1 | 7/2003 | McDevitt et al. |
| 2003/0167062 A1 | 9/2003 | Gambale |
| 2003/0187446 A1 | 10/2003 | Overaker et al. |
| 2003/0204193 A1 | 10/2003 | Gabriel |
| 2004/0181234 A1 | 9/2004 | McDevitt |
| 2004/0220573 A1 | 11/2004 | McDevitt |
| 2005/0033364 A1 | 2/2005 | Gregoire |
| 2005/0055052 A1 | 3/2005 | Lombardo |
| 2005/0090862 A1 | 4/2005 | McDevitt et al. |
| 2005/0149122 A1 | 7/2005 | McDevitt |
| 2005/0216059 A1 | 9/2005 | Bonutti |
| 2006/0079904 A1 | 4/2006 | Thal |
| 2006/0161159 A1 | 7/2006 | Dreyfuss |
| 2006/0235413 A1 | 10/2006 | Denham |
| 2006/0264951 A1 | 11/2006 | Nelson |
| 2006/0282081 A1 | 12/2006 | Fanton |
| 2007/0038230 A1 | 2/2007 | Stone |
| 2007/0142846 A1 | 6/2007 | Catanese |
| 2007/0219557 A1 | 9/2007 | Bourque |
| 2008/0033460 A1 | 2/2008 | Ziniti |
| 2008/0033486 A1 | 2/2008 | Whittaker |
| 2009/0099598 A1 | 4/2009 | McDevitt |
| 2009/0248068 A1 | 10/2009 | Lombardo |
| 2009/0318964 A1 | 12/2009 | Lombardo |
| 2009/0326579 A1 | 12/2009 | Anderhub |
| 2011/0152929 A1 | 6/2011 | McDevitt et al. |

FOREIGN PATENT DOCUMENTS

| | | |
|---|---|---|
| DE | 3406961 | 9/1985 |
| DE | 198520206 | 2/1986 |
| EP | 58744 | 9/1982 |
| EP | 124489 | 11/1984 |
| EP | 241240 | 10/1987 |
| EP | 251583 | 1/1988 |
| EP | 260970 | 3/1988 |
| EP | 270704 | 6/1988 |
| EP | 340159 | 11/1989 |
| EP | 232049 | 3/1990 |
| EP | 409364 | 1/1991 |
| EP | 574707 | 12/1993 |
| EP | 390613 | 8/1994 |
| EP | 611557 | 8/1994 |
| EP | 589306 | 8/1999 |
| EP | 1 206 924 | 5/2002 |
| EP | 1206924 | 5/2002 |
| EP | 1 844 715 | 10/2007 |
| EP | 1844715 | 10/2007 |
| FR | 2054731 | 5/1971 |
| FR | 2346591 | 10/1977 |
| FR | 2622430 | 5/1989 |
| FR | 2 682 867 | 4/1993 |
| FR | 2682867 | 4/1993 |
| GB | 2084468 | 4/1982 |
| GB | 2248778 | 4/1992 |
| JP | 5512951 B2 | 5/1980 |
| JP | 11-503931 | 4/1994 |
| JP | 6-505888 | 7/1994 |
| JP | 2000120628 | 4/2000 |
| JP | 2001-501112 | 1/2001 |
| JP | 2001-161883 | 6/2001 |
| JP | 2002-177286 | 6/2002 |
| JP | 2002-282258 | 10/2002 |
| JP | 2004-160177 | 6/2004 |
| JP | 2005-110984 | 4/2005 |
| JP | 2005-511189 | 4/2005 |
| JP | 2005-523103 | 8/2005 |
| WO | WO 8809157 | 12/1988 |
| WO | WO 8901767 | 3/1989 |
| WO | WO 9204874 | 4/1992 |
| WO | WO 9502998 | 2/1995 |
| WO | WO 9515726 | 6/1995 |
| WO | WO 9529636 | 11/1995 |
| WO | WO 9602193 | 2/1996 |
| WO | WO 9729693 | 8/1997 |
| WO | WO 9838938 | 9/1998 |
| WO | 9922648 | 5/1999 |
| WO | WO 9922648 | 5/1999 |
| WO | WO 0106909 | 9/2001 |
| WO | 03049620 | 6/2003 |
| WO | WO 03049620 | 6/2003 |
| WO | WO 2005/102190 | 5/2006 |
| WO | 2006128092 | 11/2006 |
| WO | WO 2006128092 | 11/2006 |

OTHER PUBLICATIONS

European Search Report Application No. 07253061.1 dated Mar. 10, 2008.

European Search Report Application No. 07253063.7 dated Nov. 29, 2007.

Japanese Office Action for Application No. 2007-203527, issued Jun. 5, 2012 (English translation).

Japanese Office Action for Application No. 2007-203520, issued Jun. 5, 2012 (English translation).

Supplementary Partial EP Search Report for App. No. 00950502.5 dated May 16, 2008.

(56) References Cited

OTHER PUBLICATIONS

Japanese Official Action for JP Application No. 2001-351434, prepared Oct. 10, 2007.
JP Application No. 2001-351434 Office Action dated Oct. 12, 2007.

* cited by examiner

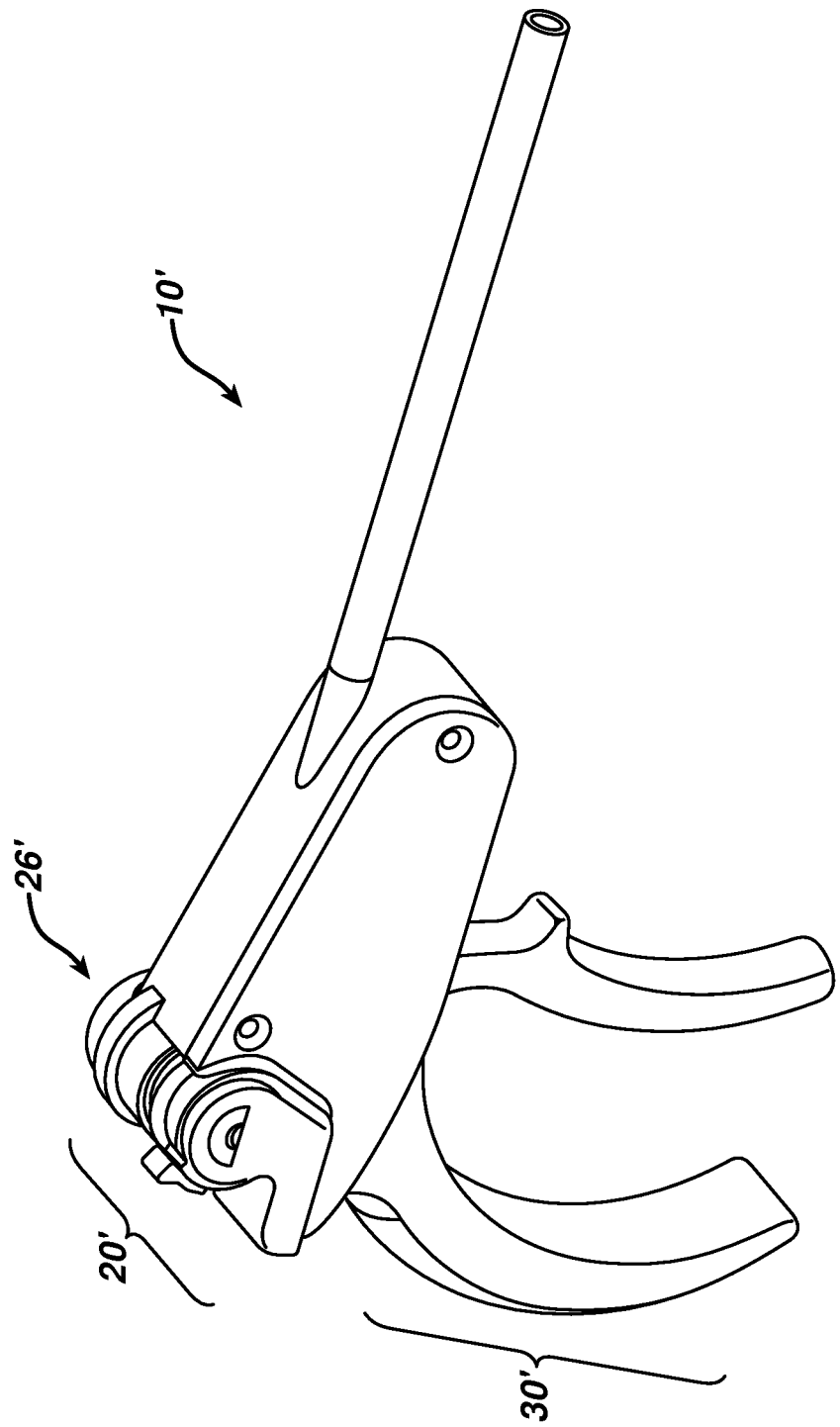

SUTURE ANCHOR SYSTEM WITH TENSION RELIEF MECHANISM

FIELD OF THE INVENTION

This invention relates generally to medical devices and procedures. More particularly, this invention relates to systems and methods for attaching soft tissue to bone.

BACKGROUND OF THE INVENTION

The complete or partial detachment of ligaments, tendons and/or other soft tissues from their associated bones within the body are relatively commonplace injuries, particularly among athletes. Such injuries are generally the result of excessive stresses being placed on these tissues. By way of example, tissue detachment may occur as the result of an accident such as a fall, over-exertion during a work-related activity, during the course of an athletic event, or in any one of many other situations and/or activities.

In the case of a partial detachment, the injury will frequently heal itself, if given sufficient time and if care is taken not to expose the injury to further undue stress. In the case of complete detachment, however, surgery may be needed to re-attach the soft tissue to its associated bone or bones. Numerous devices are currently available to re-attach soft tissue to bone. Examples of such currently-available devices include screws, staples, suture anchors and tacks. In soft tissue re-attachment procedures utilizing screws, the detached soft tissue is typically moved back into its original position over the bone. Then the screw is screwed through the soft tissue and into the bone, with the shank and head of the screw holding the soft tissue to the bone. Similarly, in soft tissue re-attachment procedures utilizing staples, the detached soft tissue is typically moved back into its original position over the bone. Then the staple is driven through the soft tissue and into the bone, with the legs and bridge of the staple holding the soft tissue to the bone.

In soft tissue re-attachment procedures utilizing suture anchors, an anchor-receiving hole is generally first drilled in the bone at the desired point of tissue re-attachment. Then a suture anchor is deployed in the hole using an appropriate installation tool. This effectively locks the suture to the bone, with the free end(s) of the suture extending out of the bone. Next, the soft tissue is moved into position over the hole containing the deployed suture anchor. As this is done, the free end(s) of the suture is (are) passed through or around the soft tissue, so that the free end(s) of the suture reside(s) on the far (i.e., non-bone) side of the soft tissue. Finally, the suture is used to tie the soft tissue securely to the bone.

Alternatively, in some soft tissue re-attachment procedures utilizing suture anchors of the type described above, the soft tissue may first be moved into position over the bone. Then, while the soft tissue lies in position against the bone, a single hole may be drilled through the soft tissue and into the bone. Next, a suture anchor is passed through the soft tissue and deployed in the bone using an appropriate installation tool. This results in the suture anchor being locked to the bone, with the free end(s) of the suture extending out of the bone and through the soft tissue. Finally, the suture is used to tie the soft tissue securely to the bone. In some cases, the suture anchor may include drill means at its distal end, whereby the suture anchor can be drilled into the bone, or drilled through the soft tissue and into the bone, whereby the aforementioned drilling and anchor-deployment steps are effectively combined.

Similarly, in soft tissue re-attachment procedures utilizing tacks, the detached soft tissue is typically moved back into its original position over the bone, and then a tack-receiving hole is generally drilled through the soft tissue and into the bone. Then the tack is driven through the soft tissue and into the bone, so that the shaft and head of the tack will hold the soft tissue to the bone.

While systems and method based on the aforementioned screws, staples, suture anchors and tacks are generally effective, they also all suffer from one or more disadvantages. Accordingly, there remains a need for improved methods and devices for attaching soft tissue to bone.

SUMMARY OF THE INVENTION

The present invention provides various methods and device for attaching soft tissue to bone. In one embodiment, an anchor insertion device is provided and includes a housing having an outer shaft extending distally therefrom and configured to receive an anchor insertion assembly, and a suture retaining element formed on the housing and configured to retain a suture coupled to a suture anchor mated to a distal end of an anchor insertion assembly. A handle assembly is slidably coupled to the housing and it is configured to engage an anchor insertion assembly disposed through the outer shaft and the housing such that the handle assembly and anchor insertion assembly are slidably movable relative to the housing and outer shaft to thereby deploy a suture anchor coupled to a distal end of the anchor insertion assembly.

The handle assembly can have various configurations, but in one embodiment it can include a trigger pivotally coupled thereto and configured to pivot to slidably move the handle assembly relative to the housing. A gear mechanism can be disposed within the handle assembly such that pivotal movement of the trigger is effective to actuate the gear mechanism to slidably move the handle assembly relative to the housing. In an exemplary embodiment, the gear mechanism is adapted to slidably move the handle assembly in a proximal direction relative to the housing.

The suture retaining element can also have a variety of configurations, but in one embodiment it can include a suture tensioning assembly adapted to tension a suture extending between a suture anchor and the suture tensioning assembly. The suture tensioning assembly can include, for example, a wheel rotatably coupled to the housing and a ratchet mechanism for allowing rotation of the wheel in a fixed direction to allow suture disposed there around to be tensioned, and for preventing rotation of the wheel in a second, opposite direction. The device can also include a lever coupled to the suture tensioning assembly and configured to release the ratchet mechanism to allow free rotation of the wheel in the second, opposite direction.

In another embodiment, a suture anchor assembly is provided and includes a suture anchor having an insert with a suture mated thereto, and a sleeve disposable over the insert and configured to lock the suture between the insert and the sleeve. The suture anchor assembly can also include a deployment device having a housing with a suture tensioning element mated to the suture for tensioning the suture between the insert and the suture tensioning element, and an actuation mechanism movably coupled to the housing and having a distal end mated to the sleeve such that the actuation mechanism is configured to position the sleeve over the insert while the suture remains fixed between the tensioning element and the insert. The suture anchor assembly can also include an inserter shaft extending through the housing and having a proximal end coupled to the actuation mechanism and a distal end coupled to the sleeve. In certain exemplary embodiments, the inserter shaft can extend through an outer shaft extending distally from the housing. The suture anchor assembly can also include a pusher slidably disposed around the inserter shaft and located between a distal end of the outer shaft and a proximal end of the insert. In other embodiments, the actuation mechanism can be slidably movable relative to the housing such that the actuation mechanism and anchor insertion assembly slide relative to the housing and outer shaft to position the sleeve over the insert. The actuation mechanism can be, for example, a handle assembly having a trigger pivotally coupled thereto such that pivoting movement of the trigger is effective to move the handle assembly relative to the housing.

Exemplary methods for deploying a suture anchor are also provided. In one embodiment, the method can include inserting a suture anchor coupled to a distal end of a deployment device into bone, coupling suture between an inner component of the suture anchor and a suture retaining element located on a housing of the deployment device, and actuating a handle assembly to position an outer component of the suture anchor over the inner component of the suture anchor thereby locking the suture between the inner and outer components. The housing and inner component can remain in a substantially fixed position relative to one another as the handle assembly is actuated such that tension applied to the suture extending between the inner component and the housing remains substantially fixed. In certain exemplary embodiments, the handle assembly can slide proximally relative to the housing when the handle assembly is actuated. Actuating the handle assembly can include pivoting a trigger coupled to the handle assembly. In another embodiment, the suture retaining element can be a suture tensioning assembly, and the method can include actuating the suture tensioning assembly to tension the suture between the suture tensioning assembly and the inner component of the suture anchor.

In other aspects, a method for deploying a suture anchor is provided and includes inserting a suture anchor coupled to a distal end of a deployment device into bone, tensioning a suture coupled to a first component of the suture anchor, and actuating a handle assembly to slide the handle assembly relative to the housing of the deployment device, thereby mating a second component of the suture anchor with the first component of the suture anchor to lock the suture between the first and second components. In one exemplary embodiment, the second component is pulled over the first component when the handle assembly is actuated. In another embodiment, tensioning the suture can include coupling the suture between the first component of the suture anchor and a suture retaining element located on a housing of the deployment device. In other aspects, the suture retaining element, first component, and suture can remain in a substantially fixed position as the handle assembly is slid relative to the housing. In yet another embodiment, the suture retaining element can be, for example, a suture tensioning assembly and the method can include tensioning the suture between the first component of the suture anchor and the suture tensioning assembly.

The present invention also provides various suture anchor devices. In one embodiment, a suture anchor device is provided having an insert with a sidewall extending between leading and trailing ends and defining an inner lumen extending through the insert, and at least one bore formed in the sidewall and configured to receive a suture therethrough. The suture anchor device also includes an outer sleeve disposable over the insert and configured to lock a suture between the outer sleeve and the insert. The insert and the outer sleeve can include a snap-lock engagement mechanism formed there between for locking the insert and the outer sleeve together.

While various snap-lock engaging mechanism can be used, in one embodiment the device can include at least one pin formed on at least one of the insert and the outer sleeve, and at least one complementary bore formed in the other one of the insert and the outer sleeve. The device can also include other features, such as an alignment mechanism formed between the insert and the outer sleeve and configured to rotationally align the insert and the outer sleeve during insertion of the outer sleeve over the insert. The alignment mechanism can be, for example, at least one protrusion formed on at least one of the insert and the outer sleeve, and at least one complementary detent formed in the other one of the insert and the outer sleeve. In another embodiment, the insert can include a plurality of detents formed adjacent to the leading end of the insert, and the outer sleeve can include a plurality of protrusions formed adjacent to a trailing end of the outer sleeve and configured to sit within the plurality of detents formed on the insert for rotationally aligning the insert and outer sleeve. The trailing end of the insert can optionally be flared and it can be configured to frictionally engage a trailing end of the outer sleeve. The trailing end of the insert can also optionally include a notch formed therein and configured to receive a corresponding protrusion formed on an inserter shaft for rotationally aligning the insert with the inserter shaft. In other embodiments, the insert and the outer sleeve can have a modulus of elasticity that is substantially the same as one another.

In yet another embodiment, a suture anchor assembly is provided and includes a hollow insert having at least one bore formed therein and configured to receive a suture therethrough, an outer sleeve disposable over the insert and configured to lock a suture between the outer sleeve and the insert, and an inserter shaft having a distal end extending through the insert and removably mated to the outer sleeve. The inserter shaft can include a pusher slidably disposed thereon and configured to abut against a proximal end of the insert to allow the pusher and inserter shaft to be moved relative to one another to position the outer sleeve over the hollow. The proximal end of the insert and a distal end of the pusher can optionally include an alignment mechanism formed there between and configured to rotationally align the insert with the pusher. In another embodiment, the insert and the outer sleeve can include a snap-lock engagement mechanism formed there between for locking the insert and the outer sleeve together. The snap-lock engaging mechanism can be, for example, at least one pin formed on at least one of the insert and the outer sleeve, and at least one complementary bore formed in the other one of the insert and the outer sleeve. The trailing end of the insert can also optionally be flared and configured to frictionally engage a trailing end of the outer sleeve.

In another embodiment, a method for anchoring suture in bone is provided and includes inserting a suture anchor coupled to a distal end of an inserter shaft into bone such that a suture coupled to an insert of the suture anchor extends from the bone, and moving the inserter shaft and a pusher slidably disposed around the inserter shaft relative to one another to position a sleeve of the suture anchor around the insert to lock the suture there between. The insert and sleeve can lock together using a snap-lock connection. Locking the insert and the sleeve can include positioning at least one protrusion formed on at least one of the insert and the sleeve within at least one corresponding bore formed in the other one of the insert and the sleeve to snap-lock the insert and sleeve together. In certain exemplary embodiments, the pusher is maintained in a fixed position as the inserter shaft is retracted relative to the pusher. Alternatively, the inserter shaft can be maintained in a fixed position as the pusher is advanced relative to the inserter shaft.

The method can also include, prior to moving the inserter shaft and pusher, tensioning the suture extending from the bone. For example, the suture can be tensioned by coupling the suture extending from the bone to a suture tensioning assembly to tension the suture between the suture tensioning assembly and the insert. The tension applied to the suture can be maintained at a substantially fixed tension when the sleeve is positioned over the insert.

BRIEF DESCRIPTION OF THE DRAWINGS

The invention will be more fully understood from the following detailed description taken in conjunction with the accompanying drawings, in which:

FIG. 6A is a perspective view of another embodiment of a deployment device;

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention generally provides methods and devices for attaching soft tissue to bone. In general, a deployment device, insertion assembly, and suture anchor are provided. The insertion assembly is coupled between the deployment device and the suture anchor to allow the deployment device to deploy the suture anchor into bone. A person skilled in the art will appreciate that each of the various components disclosed herein can be used alone, in combination with one another, or in combination with various other devices.

Figure 1:
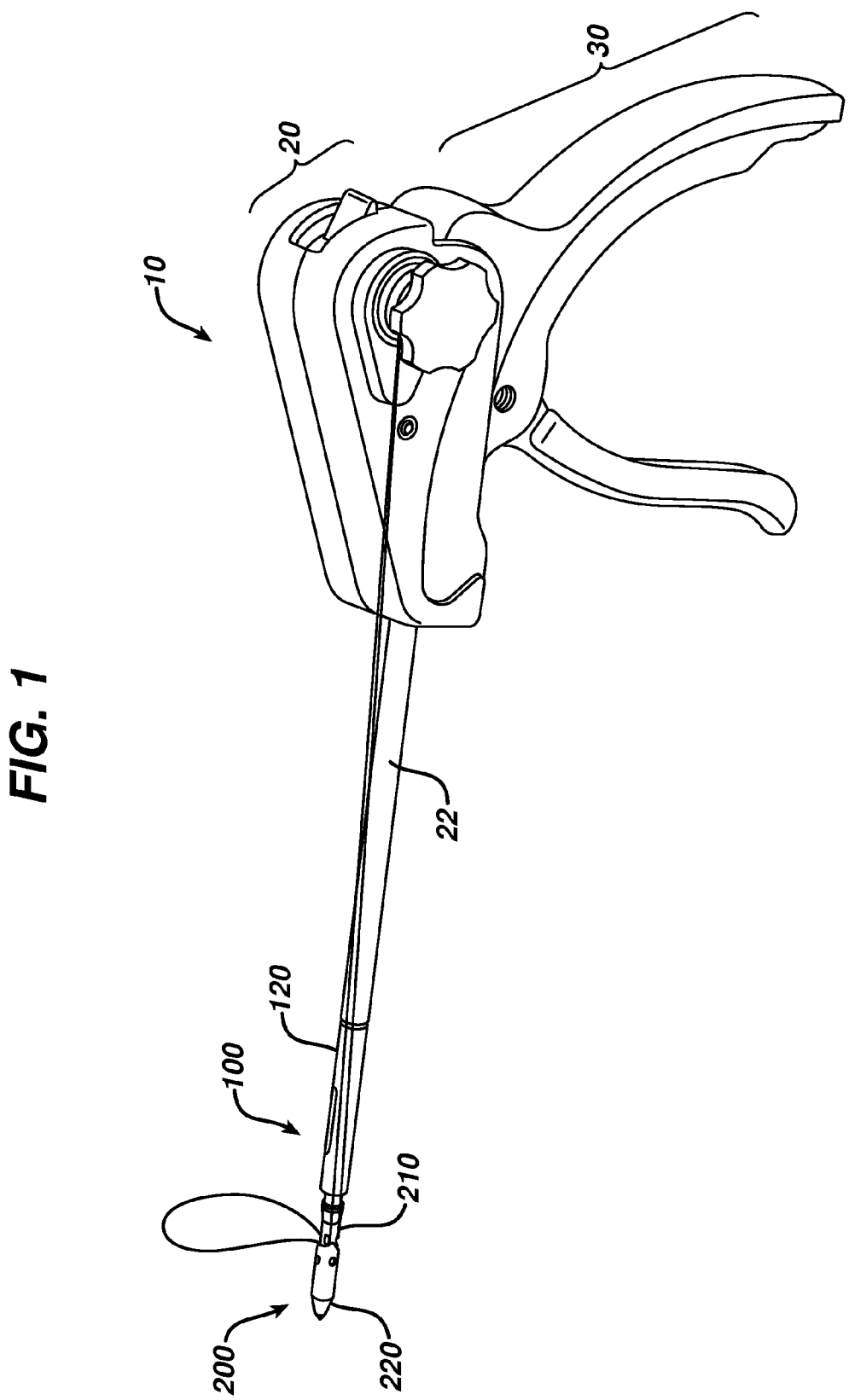
FIG. 1 is a perspective view of one embodiment of a suture anchor deployment device, insertion assembly, and a suture anchor.
Figure 2:
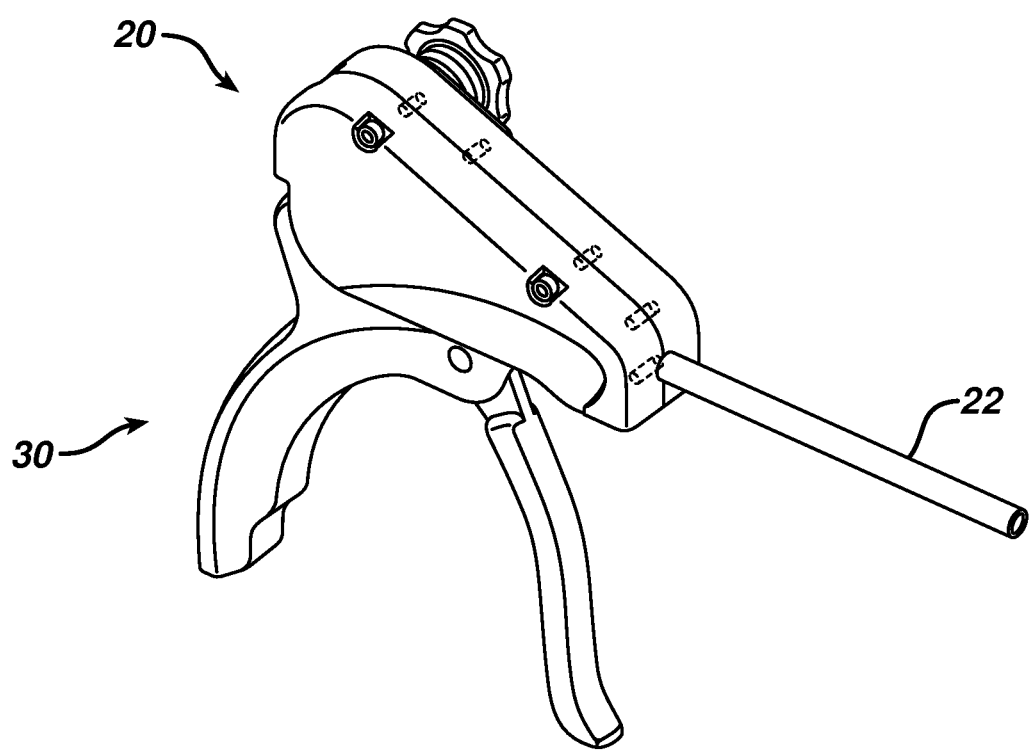
FIG. 2 is a perspective view of the deployment device of FIG. 1.
Figure 3:
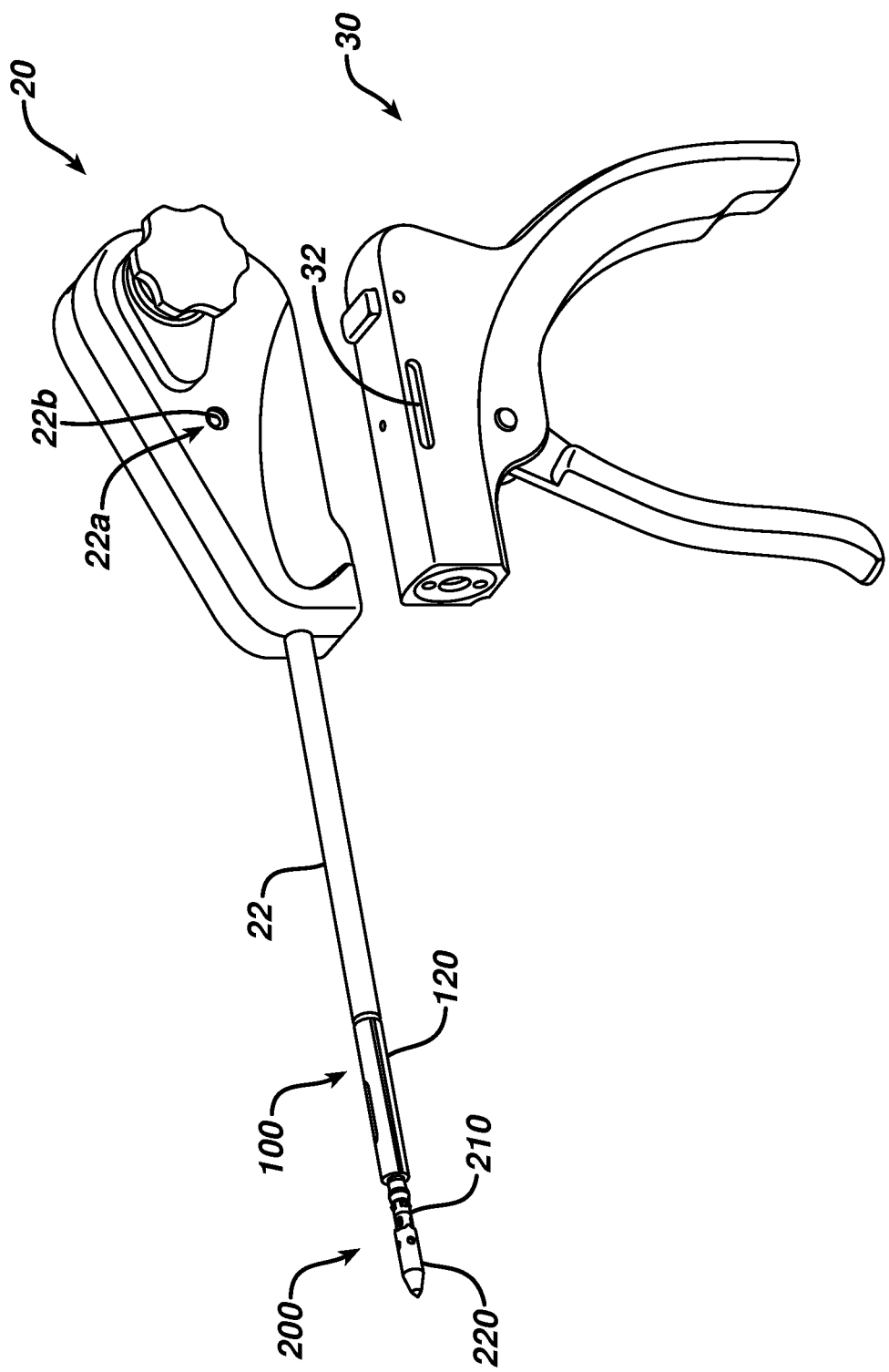
FIG. 3 is a partially exploded view of the deployment device of FIG. 2, showing first and second portions that slidably move relative to one another.

FIG. 1 generally illustrates one exemplary embodiment of a suture anchor deployment device 10 having an insertion assembly 100 coupled thereto and extending therefrom, and having a suture anchor 200 coupled to a distal end of the insertion assembly 100. The deployment device 10, which is shown in more detail in FIGS. 2 and 3, generally includes a housing 20 having an outer shaft 22 extending distally therefrom for receiving the insertion assembly 100, and a handle assembly 30 coupled to the housing 20 and configured to engage the insertion assembly 100. The handle assembly 30 and the insertion assembly 100 can move together relative to the housing 20 and outer shaft 22 to deploy a suture anchor 200 coupled to a distal end of the anchor insertion assembly 100. While the type of movement between the housing 20 and the handle assembly 30 can vary, in an exemplary embodiment the housing 20 and handle assembly 30 are slidably movable relative to one another. FIG. 3 illustrates the housing 20 and handle assembly 30 separated from one another. As shown, the handle assembly 30 can include one or more slots formed in a sidewall thereof. FIG. 3 illustrates one slot 32 formed in the sidewall thereof, however a second slot can be formed in the opposed sidewall. The housing 20 can include one or more corresponding bores formed therein and each bore can receive a pin configured to be slidably disposed within a slot. FIG. 3 illustrates a bore 22a formed in a sidewall of the housing 20 and having a pin 22b disposed therein. The pin(s) and slot(s) will thus guide sliding movement between the housing 20 and handle assembly 30 in proximal and distal directions. In an exemplary embodiment, actuation of the handle assembly 30 causes the housing 20 to move in a proximal direction and/or the handle assembly 30 to move in a distal direction.

Referring back to FIG. 1, the suture anchor 200 that is coupled to the insertion assembly 100 generally includes an insert 210 and a sleeve 220 that is disposable over the insert 210. The sleeve 220 is coupled to an inserter shaft 110 (FIG.

10) of the insertion assembly 100, and the insert 210 is slidably disposed around the inserter shaft and it abuts against a pusher 120 positioned proximally adjacent thereto and also slidably disposed around the inserter shaft. The pusher 120 is positioned just distal of the outer shaft 22 that extends distally from the housing 20. As a result, actuation of the handle assembly 30 will cause the handle assembly 30 to move proximally, pulling the inserter shaft and sleeve 220 proximally. The outer shaft 22 of the housing 20 will abut against the pusher 120 on the insertion assembly 100, and the pusher 120 in turn will abut against the insert 210 to maintain the insert 210 in a substantially fixed position while the sleeve 220 is being pulled there over by the inserter shaft and handle assembly 30. Once the sleeve 220 is disposed over the insert 210, a suture coupled to the anchor 200 will be engaged between the sleeve 210 and insert 210. The suture can be mated to tissue, allowing the tissue to be anchored to bone within which the suture anchor 200 is disposed.

A person skilled in the art will appreciate that movement of the housing 20 and handle assembly 30 is relative to each other, and that the direction of movement of each component as described and claimed herein is not intended to be limiting in any way. That is, the housing 20 can remained fixed while the handle assembly 30 moves, the handle assembly 30 can remain fixed while the housing 20 moves, or both components can move. The components that move can vary depending on the configuration of the suture anchor 200 and insertion assembly 100, as well as the method of use.

Figure 4:
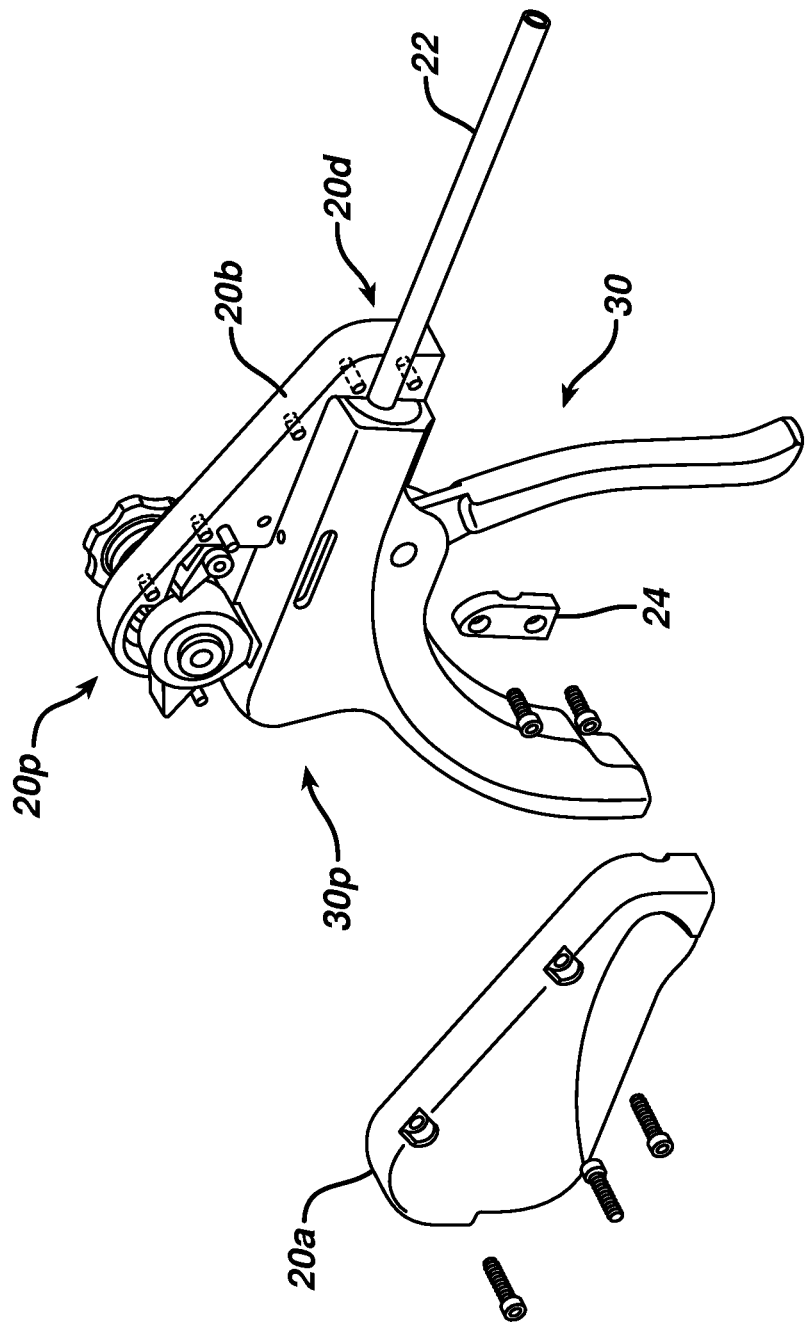
FIG. 4 is a partially exploded perspective view of the deployment device of FIG. 2, showing a suture retaining element disposed therein.
Figure 5:
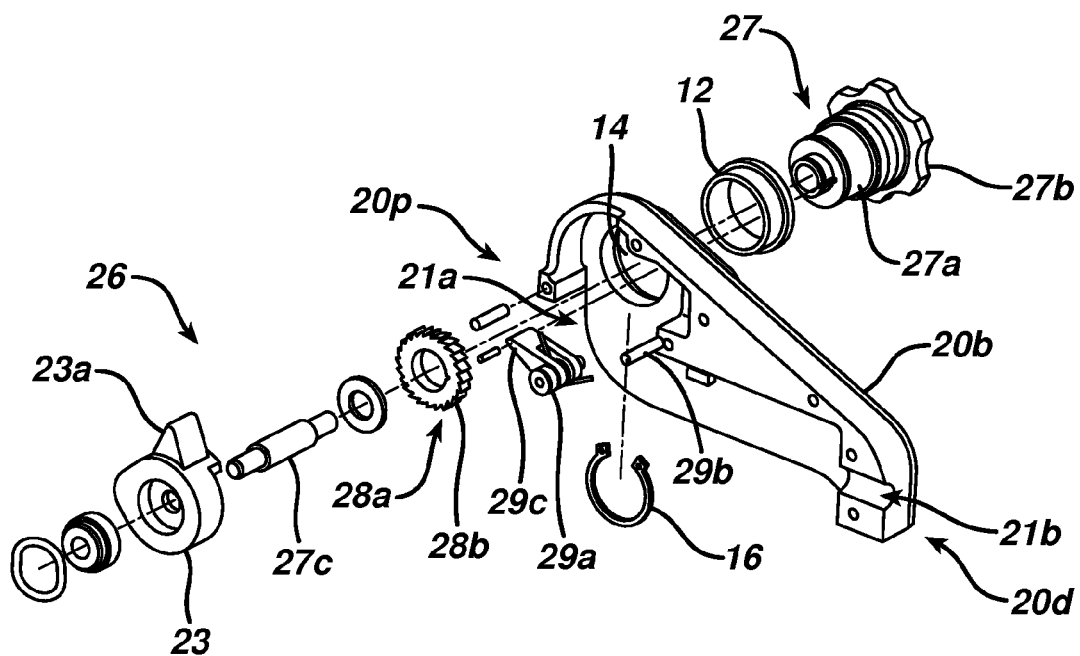
FIG. 5 is an exploded perspective view of a portion of the deployment device of FIG. 2.

The housing 20 of the deployment device 10, which is shown in FIGS. 2-5, can have a variety of configurations, but in the illustrated embodiment the housing 20 generally includes first and second opposed housing halves 20a, 20b (FIG. 4) that come together to define a generally elongate, hollow body. The housing 20 can, however, be formed from a single component, or from multiple components. An interior portion of the housing 20 can seat a portion of the handle assembly 30, which will be discussed in more detail below. In an exemplary embodiment, the housing 20 and handle assembly 30 are configured to slidably move relative to one another in a proximal-distal direction, as previously described above. Thus, as shown in FIGS. 4 and 5, the proximal end 20p of the housing 20 can include an opening 21a formed therein for slidably receiving a proximal end 30p of the handle assembly 30. The opening 21a can be formed by a cut-out formed in the proximal wall of each housing half 20a, 20b. The housing 20 can also include a generally elongate, hollow outer shaft 22 that extends through an opening 21b formed in a distal end 20d of the housing 20. In an exemplary embodiment, the outer shaft 22 is fixedly coupled to the housing 20 such that it moves in conjunction with the housing 20. The particular mating location can vary. In the embodiment shown in FIG. 4, the outer shaft 22 is configured to be fixedly captured between one of the housing halves, i.e., housing half 20b, and a clamp member 24 which is fastened to the housing half 20b at a distal end 20d of the housing 20. This allows the outer shaft 22 to move with the housing 20 without interfering with sliding movement of the handle assembly 30 relative to the housing 20.

As further shown in FIG. 4, the outer shaft 22 can also extend through a portion of the handle assembly 30 to allow a gear assembly disposed in the handle assembly 30 to engage the outer shaft 22 and slidably move the outer shaft 22 and the housing 20 relative to the handle assembly 30. The gear assembly and techniques for moving the outer shaft 22 and housing 20 relative to the handle assembly 30 will be described in more detail below with respect to FIGS. 7 and 8.

The deployment device 10 can also include a suture retaining element formed or disposed thereon and configured to mate to a suture that is coupled to a suture anchor being deployed. The suture retaining element can have a variety of configurations, and it can be in the form of a clamp, fastener, pin, or other element configured to receive and retain a suture. Regardless of the configuration, in an exemplary embodiment the suture retaining element is configured such that tension applied to a suture extending between the suture retaining element and the suture anchor will be maintained at a substantially fixed tension during deployment of the suture anchor. In the embodiment shown in FIGS. 4 and 5, this is achieved by positioning a suture retaining element on the housing 20. Since the suture extends between the insert of the suture anchor and the suture retaining element, and since the insert moves with the housing 20, the suture will move with the housing 20. As a result, the tension applied to the suture by the suture retaining element will be maintained during deployment of the suture anchor, i.e., while the sleeve is being pulled over the insert. As indicated above, the particular location of the suture retaining element can vary depending on the configuration of the deployment device, insertion assembly, and suture anchor. For example, the suture retaining element can be formed or disposed on the handle assembly 30 such that is moves in coordination with the handle assembly 30.

FIG. 5 illustrates one exemplary suture retaining element, in the form of a suture tensioning assembly 26. In general, the suture tensioning assembly 26 includes a tensioning wheel 27 that is effective to receive a suture there around such that rotation of the tensioning wheel 27 increases or decreases tension applied to the suture. The illustrated tensioning wheel 27 is in the form a cylindrical housing 27a having a knob 27b formed on one end thereof for grasping and rotating the tensioning wheel 27, and having a central shaft 27c extending therethrough. The central shaft 27c is rotatably disposed through the housing 20, and in particular through one of the housing halves, i.e., housing half 20b. As shown in FIG. 5, the device includes a bushing 12 that sits within an opening 14 formed in the housing half 20b, and that rotatably seats a portion of the tensioning wheel 27. The bushing 12 is mated to the housing half 20b using a spring clip 16 disposed there around and positioned on an interior portion of the housing half 20b. The suture tensioning assembly 26 can also include a mechanism for maintaining the tensioning wheel 27 in a desired rotated position. As shown in FIG. 5, the tensioning assembly 26 includes a pawl and ratchet mechanism that is coupled to the shaft 27c of the tensioning wheel 27. The ratchet mechanism is in the form of a wheel 28a that is disposed around the shaft 27c and that includes teeth 28b formed there around, and a pawl 29a that rotatably mates to the housing half 20b, e.g., using a post 29b formed on an interior of the housing half 20b, and that includes an arm 29c that is configured to engage the teeth 28b formed around the ratchet 28a. In use, a length of suture can be wrapped around the tensioning wheel 27 to mate the suture to the wheel 27. When the wheel 27 is rotated in a direction that applies tension to the suture, i.e., further winds the suture around the wheel 27, the pawl 29a will engage the teeth 28b on the ratchet 28a to prevent the wheel 27 from rotating in an opposite direction, thus maintaining the wheel 27 in the desired rotated position and maintaining the tension on the suture.

The suture tensioning assembly 26 can also include a mechanism to release the tension applied to the suture, i.e., to release the pawl 29a from engagement with the teeth 28b on the ratchet 28a. In the embodiment shown in FIG. 5, the suture tensioning assembly 26 includes a cam 23 that is disposed around the ratchet 28a and that is configured to cam the pawl 29a out of engagement with the ratchet 28a to allow free rotation of the tensioning wheel 27. The cam 23 can include a lever 23a formed thereon and extending through a portion of the housing 20 to allow the user to effect movement of the cam 23. Pivotal movement of the cam 23 relative to the housing 20 can release the pawl 29a from the ratchet 28a. A person skilled in the art will appreciate that the cam and ratchet mechanism can have a variety of other configurations. Moreover, various other suture tensioning or retaining elements can be used.

Figure 6B:
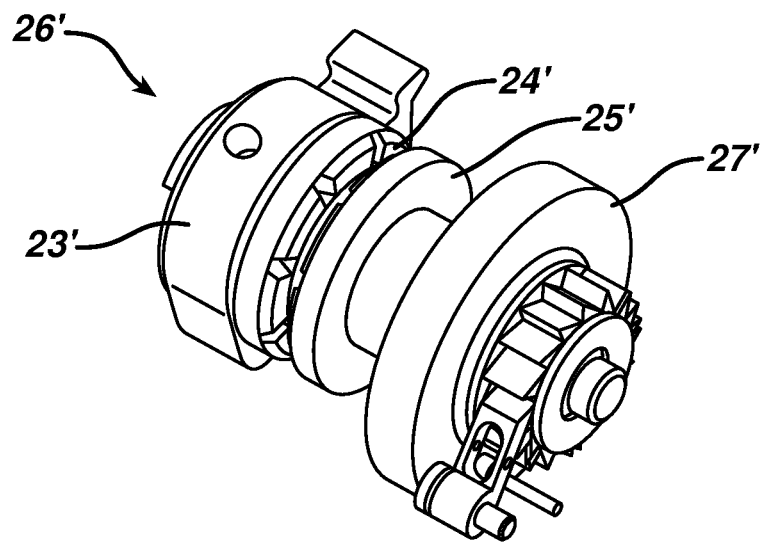
FIG. 6B is a perspective view of a suture tensioning element of the deployment device shown in FIG. 6A.
Figure 6C:
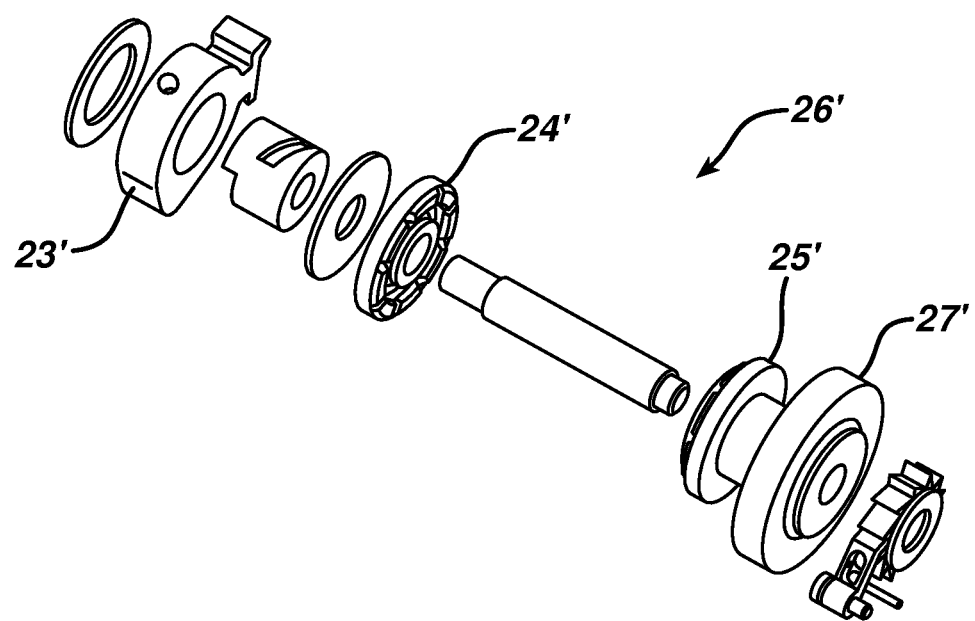
FIG. 6C is an exploded perspective view of the suture tensioning element of FIG. 6B.

FIGS. 6A-6C illustrate another exemplary embodiment of a suture retaining element. In general, FIG. 6A illustrates a deployment device 10' having a housing 20' and a handle assembly 30'. In this embodiment, the suture retaining element 26' is disposed on a back end of the housing 20', and it is configured to trap a suture, rather than have the suture would there around. In particular, referring to FIGS. 6A and 6B, the components are similar to the previous embodiment however rotation of the cam 23' causes a moving plate 24' to slide toward a stationary plate 25' to trap a suture positioned there between. Once a suture is trapped, the tensioning wheel 27' can be rotated to adjust the tension applied to the suture.

Figure 7:
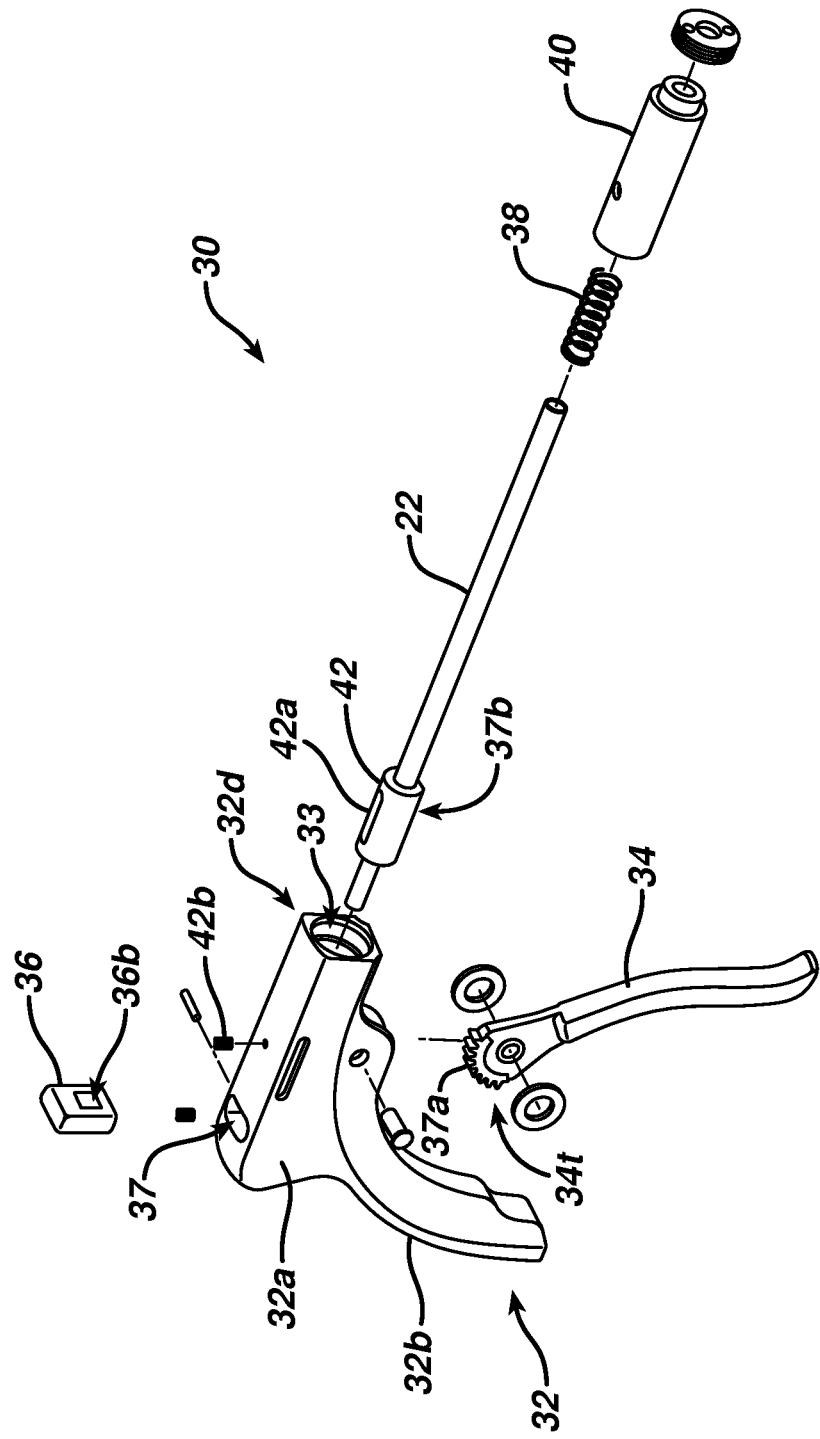
FIG. 7 is a partially exploded perspective view of a handle assembly of the deployment device of FIG. 2.
Figure 8:
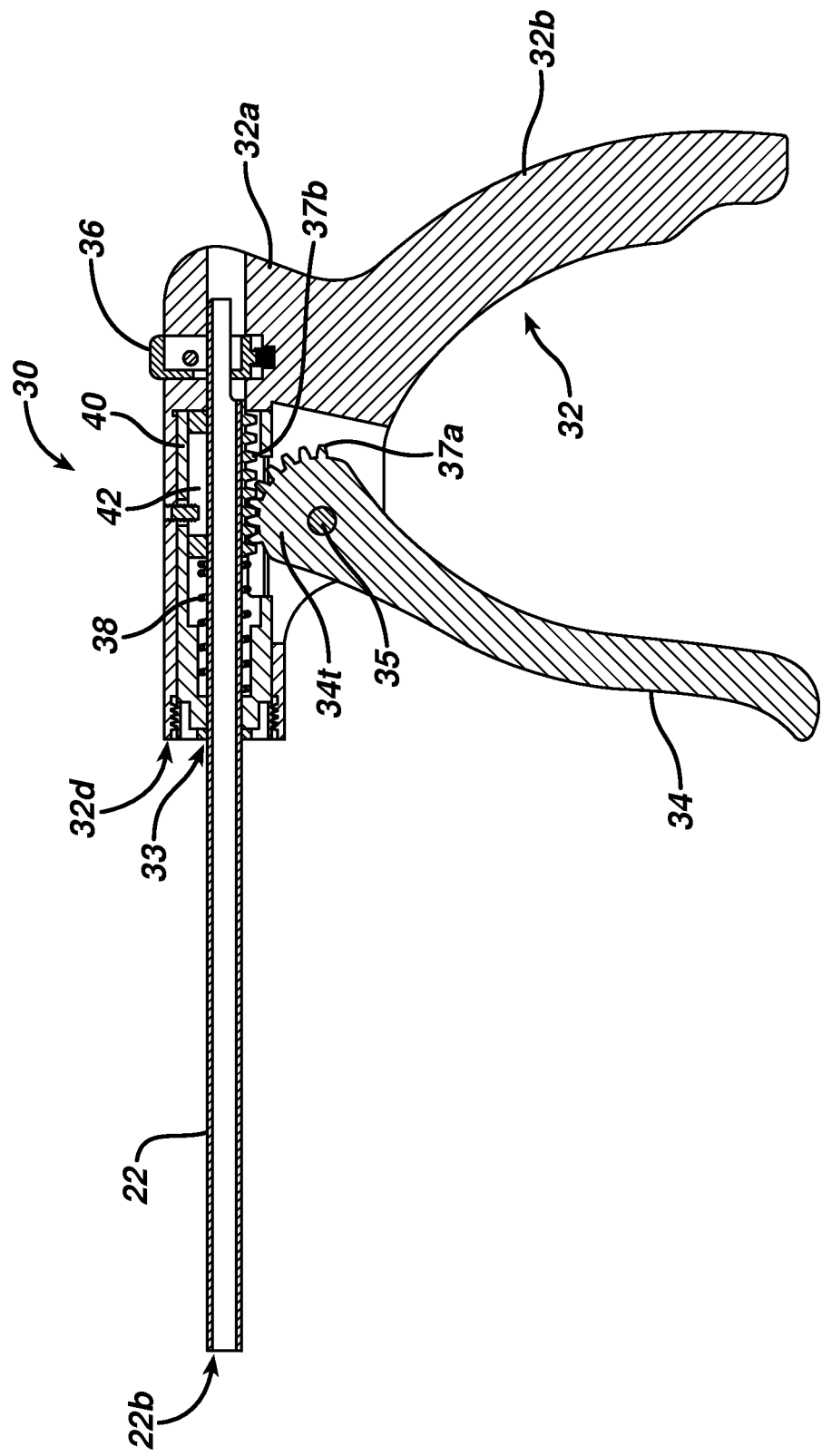
FIG. 8 is a cross-sectional view of the handle assembly of FIG. 7.

As previously indicated, the housing 20 can be slidably coupled to a handle assembly 30 that is effective, upon actuation, to deploy a suture anchor into bone. While the handle assembly 30 can have a variety of configurations, in an exemplary embodiment, as shown in FIGS. 7 and 8, the handle assembly 30 generally includes a stationary member 32 and a trigger 34 movably coupled to the stationary member 32. In this embodiment, the stationary member 32 is configured to engage an inserter shaft 110 of the insertion assembly 100 (FIG. 10), and the trigger 34 is adapted to pivot toward the stationary member 32 to slide the housing 20 relative to the handle assembly 30.

Figure 10:
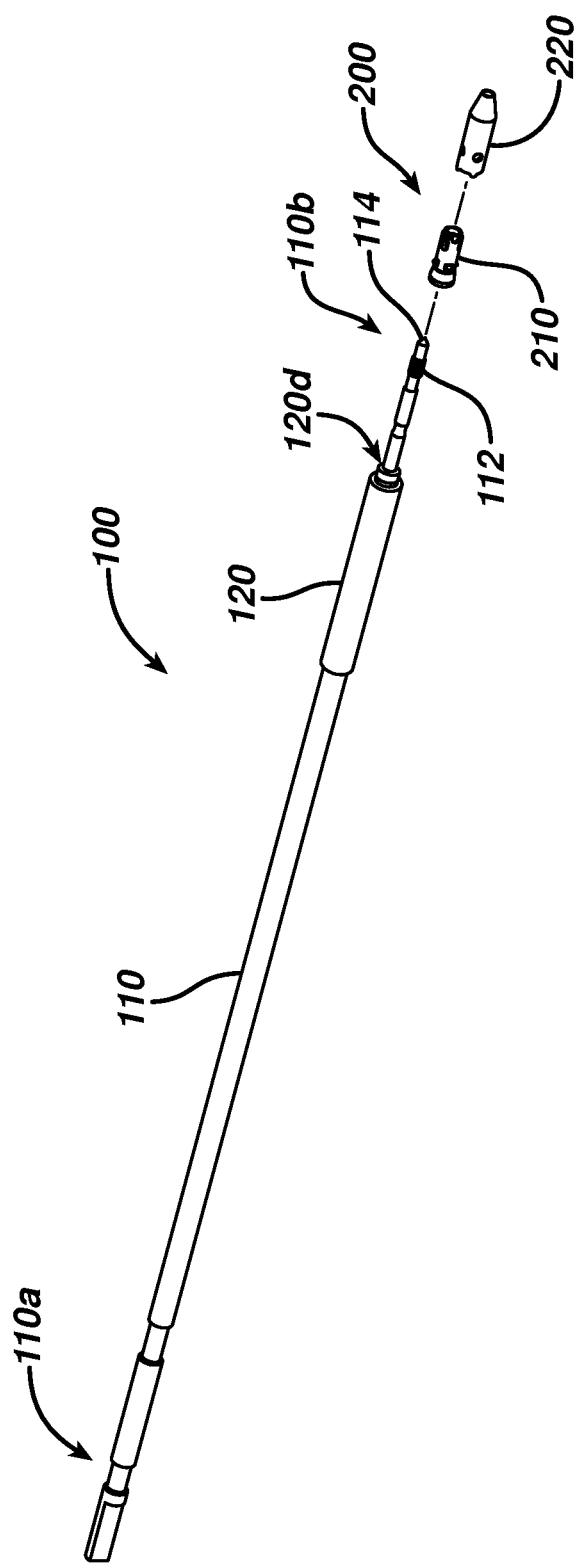
FIG. 10 is a perspective view of the insertion assembly of FIG. 1 with a suture anchor about to be attached thereto.

The stationary member 32 can have various shapes and sizes, but in one embodiment, as shown, it has a generally elongate hollow, rectangular housing portion 32a and a stationary handle 32b that extends from the housing portion 32a and that is configured to be grasped by a user. The housing portion 32a is effective to receive and mate to the inserter shaft 110 of the insertion assembly 100 (FIG. 10). In particular, the housing portion 32a can include an opening 33 formed in a distal end 32d thereof for receiving a proximal end of the inserter shaft. The housing portion 32a can also include a mating element formed thereon for removably engaging the inserter shaft. In the embodiment shown in FIGS. 7 and 8, the housing portion 32a includes a locking member 36 that is disposed through an opening 37 formed in a top surface of the housing portion 32a, and that includes a bore 36b formed therethrough for receiving the proximal end of the inserter shaft. The illustrated locking member 36 is in the form of a generally square or rectangular shaped member, however the locking mechanism can have various other shapes and sizes. The locking member 36 can also be biased, e.g., using a spring disposed within the housing portion 32a, to a locked position such that it will grasp and engage a notch formed in the proximal end of the inserter shaft to prevent the inserter shaft from being removed. In order to release the inserter shaft from the housing portion 32a, the locking member 36 can be depressed to overcome the biasing force, allowing free sliding movement of the inserter shaft relative thereto. A person skilled in the art will appreciate that a variety of other techniques can be used to mate the inserter shaft to the housing portion.

As indicated above, the handle assembly 30 can also include a trigger 34 that is movably coupled to the stationary portion 32a. While the type of movement of the trigger 34 can vary, in one embodiment the trigger 34 is pivotally coupled to the stationary portion 32a such that it moves between an open position in which the trigger 34 is spaced apart from the stationary handle 32b, as shown in FIG. 8, and a closed position in which the trigger 34 is positioned adjacent to the stationary handle 32b. In the illustrated embodiment, the trigger 34 is pivotally mated to the stationary portion 32a by a pivot pin 35. The trigger 34 can also be effective to engage the portion of the outer shaft 22 that extends through the housing portion 32a of the stationary member 32 such that movement of the trigger 34 between the open and closed positions is effective to move the outer shaft 22 between proximal and distal positions relative to the handle assembly 30. As a result, the housing 20, which is coupled to the outer shaft 22, will move with the outer shaft 22, thus allowing a suture anchor to be deployed, as will be discussed in more detail below. While various techniques can be used to allow the trigger 34 to engage and slidably move the outer shaft 22 within the housing portion 32a of the handle assembly 30, in an exemplary embodiment the handle assembly 30 includes a gear mechanism disposed therein. In the embodiment shown in FIGS. 7 and 8, the gear mechanism is in the form of a plurality of teeth 37a formed on a terminal end 34t of the trigger 34 and effective to engage corresponding teeth 37b formed on a proximal portion of the outer shaft 22, as will be discussed below. As the trigger 34 pivots from the open position to the closed position, the teeth 37a on the trigger 34 will engage the teeth 37b on the outer shaft 22 to move the outer shaft 22 in a distal direction relative to the handle assembly 30. The housing 20 (not shown) of the device 10 will thus move distally with the outer shaft 22. Or, stated another way, the handle assembly 30 and the inserter shaft (not shown) coupled thereto will move in a proximal direction relative to the housing 20 and outer shaft 22.

The trigger 34 can also be biased to the open position, such that a force must be applied to the trigger 34 to overcome the biasing force and move the trigger to the closed position, and such that release of the trigger 34 from the closed position will allow the trigger 34 to automatically return to the open position. While various techniques can be used to bias the trigger 34 to the open position, in one exemplary embodiment, as shown in FIGS. 7 and 8, a spring 38 can be disposed between a proximal portion of the outer shaft 22 and a portion of the housing portion 32a of the stationary member 32 on the handle assembly 30. In particular, the handle assembly 30 can include a hollow elongate member or barrel 40 disposed therein and configured to slidably seat a proximal housing 42 formed on or disposed around a proximal portion of the outer shaft 22. The spring 38 can be disposed within the hollow barrel 40, and a portion of the spring 38 can be positioned around a portion of the proximal housing 42 of the outer shaft 22. The teeth 37b, previously discussed above, can be formed on an inferior or bottom surface of the proximal housing 42 on the outer shaft 22, and the teeth 37b can be positioned proximal of the spring 38. Thus, the spring 38 will extend between the distal-most tooth of the proximal housing 42 of the outer shaft 22 and a distal end wall of the barrel 40, as shown in FIG. 8. The barrel 40 can also include an elongate slot or opening formed in an inferior or bottom surface thereof for receiving the terminal end 34*t* of the trigger 34.

When the trigger 34 is moved from the open position to the closed position, the proximal housing 42 on the outer shaft 22 will be moved distally, thus compressing the spring 38 between the proximal housing 42 and the distal end of the barrel 40. As a result, when the trigger 34 is released, the spring 38 will force the proximal housing 42 on the outer shaft 22 back to the proximal position, thereby causing the teeth 37*b* on the proximal housing 42 of the outer shaft 22 to engage the teeth 37*a* on the trigger 34 and pivot the trigger 34 back to the open position. As further shown in FIG. 7, the proximal housing 42 can also include a slot 42*a* formed on a superior or top surface thereof for receiving a pin 42*b* extending through the housing portion 32*a* of the stationary member 32 on the handle assembly 30. The pin 42*b* and slot 42*a* will allow the proximal housing 42 on the outer shaft 22 to slidably move proximally and distally within the housing portion 32*a* of the stationary member 32, while preventing rotation thereof to keep the teeth 37*b* on the proximal housing 42 in alignment with the teeth 37*a* on the trigger 34. A person skilled in the art will appreciate that a variety of other techniques can be used to bias the trigger 34 to an open or a closed position, as may be desired.

Figure 9A:
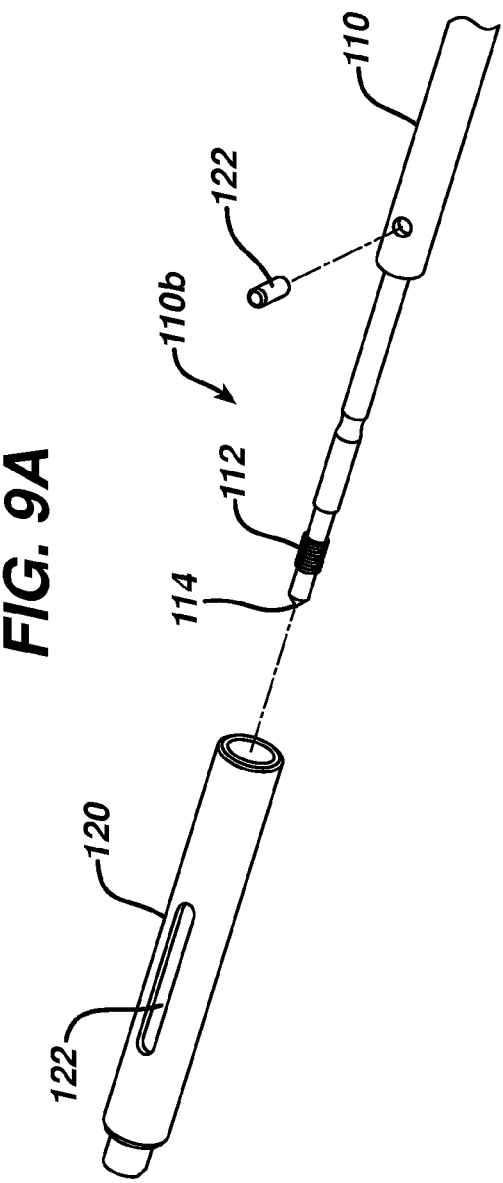
FIG. 9A is an exploded perspective view of a distal portion of an insertion assembly of the deployment device of FIG. 2.

The insertion assembly 100 is shown in more detail in FIGS. 9A-10. As shown, the insertion assembly 100 generally includes an elongate shaft, referred to herein as an inserter shaft 110, and a pusher 120 disposed around a portion of the inserter shaft 110. The inserter shaft 110 includes a proximal end 110*a* that is adapted to mate to the stationary portion 32 of the handle assembly 30, as discussed above, and a distal end 110*b* that is adapted to mate to one component of a suture anchor 200, such as a sleeve 220 as will be discussed in more detail below. While various mating techniques can be used, in one embodiment the distal end 110*b* of the inserter shaft 110 can include threads 112 formed around a portion thereof and adapted to engage corresponding threads formed within the sleeve 220. The distal end 110*b* can also include a pointed or sharpened tip 114 adapted to facilitate penetration of the insertion assembly 100 into bone.

As indicated above, the inserter shaft 110 can also include a pusher 120 disposed around a portion thereof. The pusher 120 can have various configurations, but in an exemplary embodiment it is configured to be positioned between a distal end 22*b* (FIG. 8) of the outer shaft 22 of the deployment device 10 and a proximal end of an anchor, such as a proximal end of an insert 210 of anchor 200 as will be discussed below. The pusher 120 is also preferably slidably movable along a longitudinal axis of the inserter shaft 110. This will allow the pusher 120 to advance the insert 210 into the sleeve 220, or alternatively to maintain the insert 210 in a fixed position as the sleeve 210 is pulled proximally there over. In other words, the insert 210, pusher 120, outer shaft 22, and housing 20 will move in coordination with one another relative to the sleeve 220, inserter shaft 110, and handle assembly 30 to position the insert 210 within the sleeve 220.

Figure 9B:
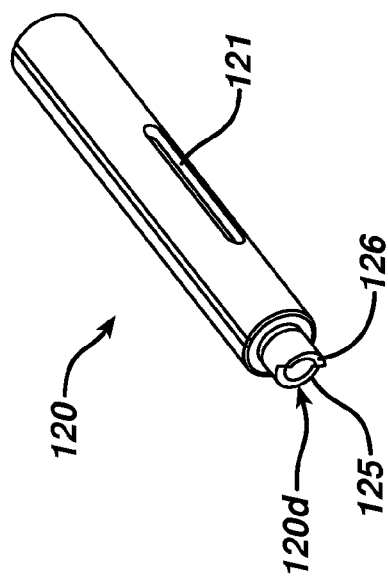
FIG. 9B is a perspective view of a pusher of the insertion assembly of FIG. 9A.

As best shown in FIGS. 9A and 9B, in one exemplary embodiment the pusher 120 can be in the form of an elongate, hollow tube that is slidably disposed around a distal portion of the inserter shaft 110. An elongate slot or cut-out 121 can be formed in the pusher 120, and a pin 122 can be disposed therethrough and mated to the inserter shaft 110 to allow slidable movement of the pusher 120 relative to the inserter shaft 110 while preventing rotation of the pusher 120 around the inserter shaft 110. Other techniques can optionally be used to slidably mate the pusher 120 to the inserter shaft 110, or alternatively the pusher 120 can merely float around the inserter shaft 110. When the pusher 120 is mated to the inserter shaft 110, as shown in FIGS. 10 and 11, the pusher 120 will be positioned just proximal to the insert 210 such that the distal end 120*d* of the pusher 120 abuts against the insert 210.

Figure 16:
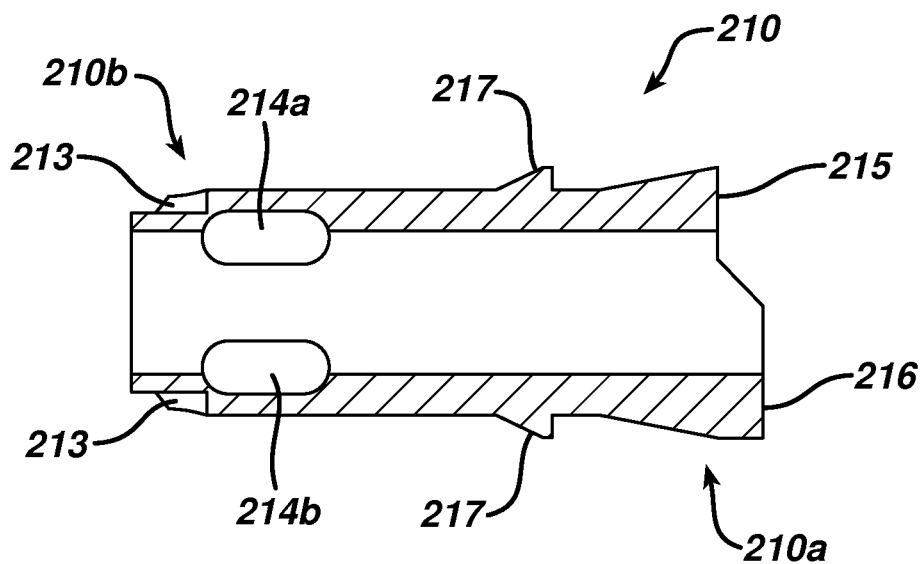
FIG. 16 is a cross-sectional view of the insert shown in FIG. 15.

The pusher 120 can also optionally include an alignment mechanism for rotationally aligning the insert 210 with the pusher 120. This can facilitate proper positioning of the insert 210 within the sleeve 220. While various alignment techniques can be used, in one exemplary embodiment the pusher 120 and/or insert 210 can include a notch or projection formed thereon and configured to be disposed within a corresponding notch or projection formed in the other one of the pusher and/or insert. For example, FIG. 9B illustrates a cut-out or notch 125 and a projection 126 formed in the distal-most end of the pusher 120. The proximal-most end of the insert 210 can have a shape that complements a shape of the distal-most end of the pusher 120, i.e., the insert 210 can include a corresponding notch 215 and projection 216 formed thereon, as shown in FIG. 16. The projection 216 on the insert 210 can rest within the notch 125 in the pusher 120 to rotationally align the insert 210 with the pusher 120.

Figure 11:
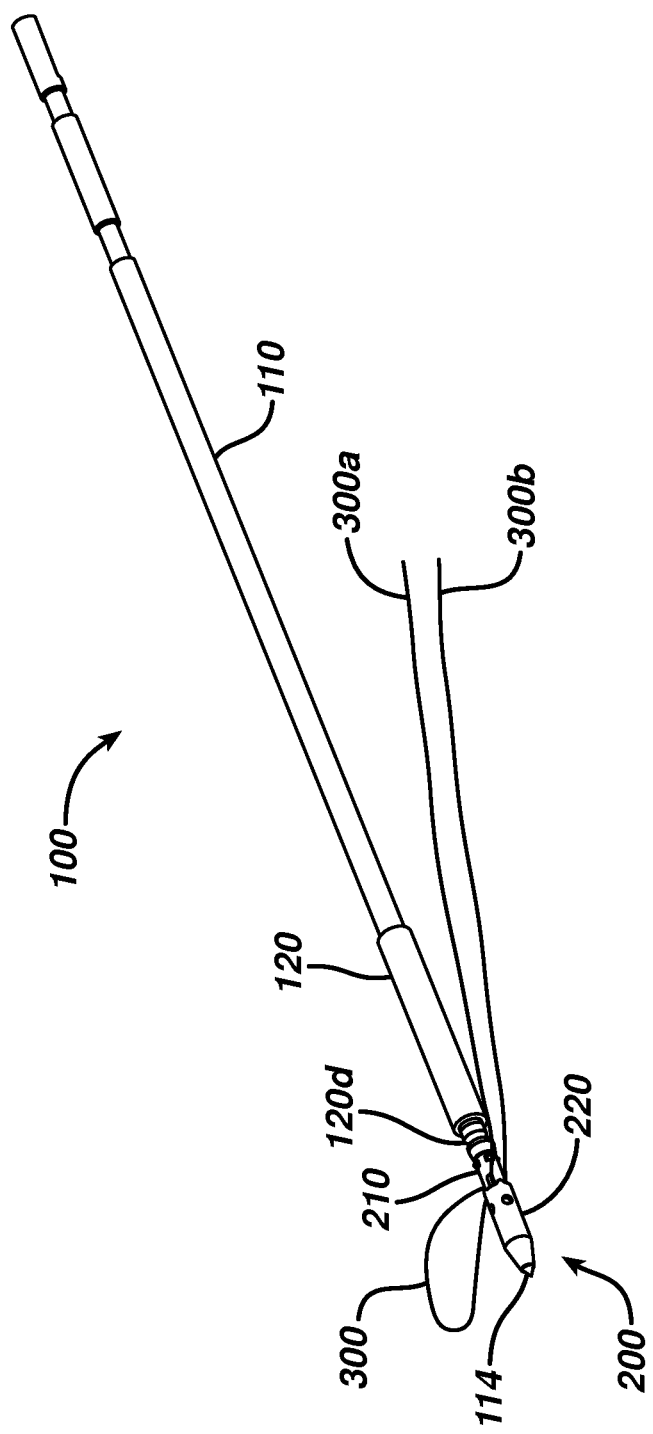
FIG. 11 is a perspective view of the insertion assembly and suture anchor of FIG. 10 fully assembled.
Figure 12:
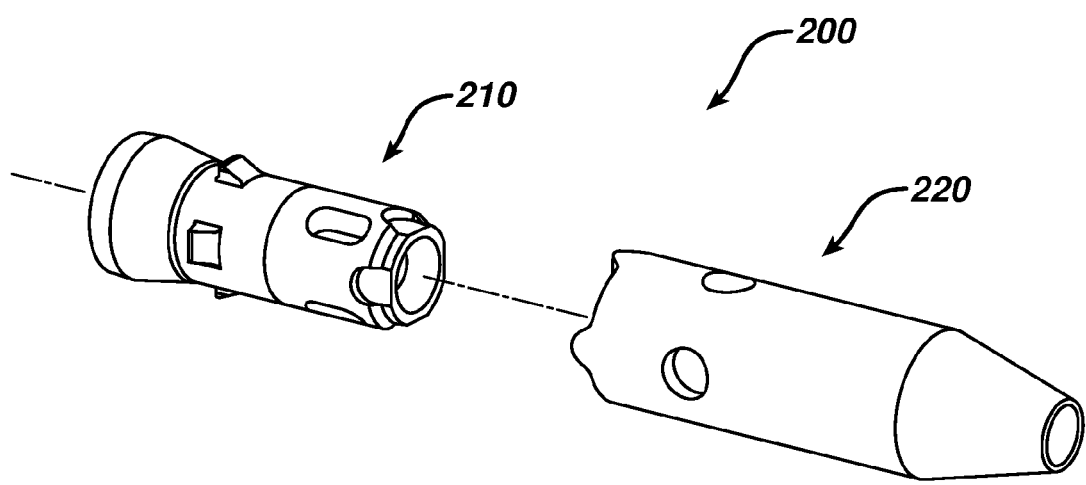
FIG. 12 is an exploded view of the suture anchor shown in FIG. 1, having a sleeve and an insert.

FIG. 11 illustrates the insertion assembly 100 fully assembled and mated to a suture anchor 200. While various suture anchors known in the art can be used with the insertion assembly 100 and deployment device 10, in the illustrated embodiment the suture anchor 200 generally includes an outer sleeve 220 that is adapted to be disposed within a bone tunnel, and an insert 210 that is adapted to be disposed within the outer sleeve 220. The sleeve 220 and insert 210 are shown in more detail in FIGS. 12-16. In general, the insert 210 can be configured to mate to a suture such that the suture will be locked between the insert 210 and outer sleeve 220 when the insert 210 is disposed within the outer sleeve 220. The insert 210 can also be configured to cause at least a portion of the outer sleeve 220 to deformably expand to lock the outer sleeve 220 within the bone tunnel.

Figure 13:
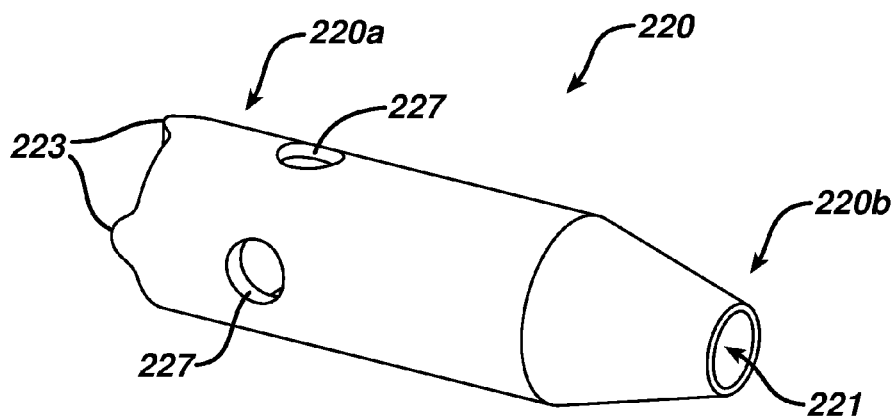
FIG. 13 is a perspective view of the sleeve of the suture anchor of FIG. 12.
Figure 14:
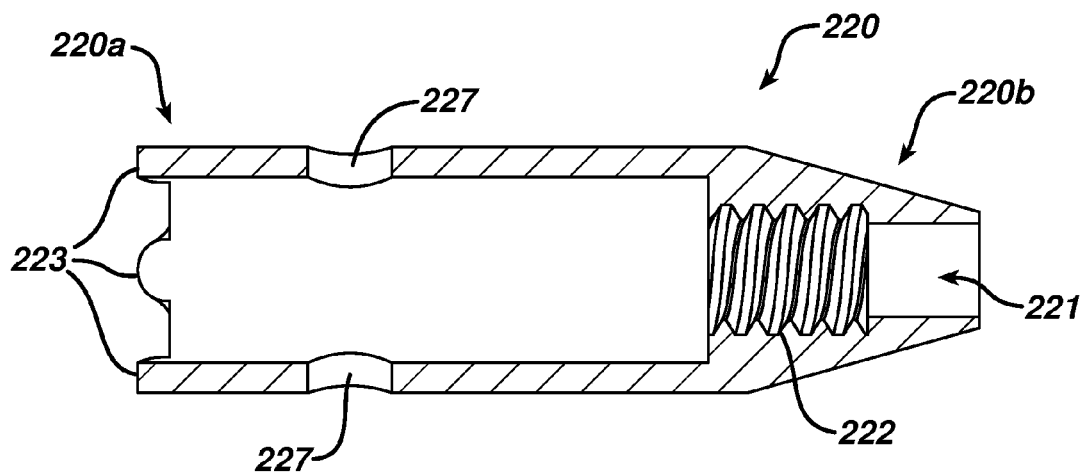
FIG. 14 is a cross-sectional view of the sleeve shown in FIG. 13.

Referring to FIGS. 13 and 14, the outer sleeve 220 of the suture anchor 200 can have a generally elongate hollow configuration with a leading distal end 220*b* and a proximal trailing end 220*a*. The distal end 220*b* can have various shapes and sizes, and it can include a bone-penetrating tip formed thereon, or alternatively it can include a bore or opening 221 formed therein as shown for allowing the tip of the inserter shaft 110 (FIG. 10) to penetrate therethrough and guide the distal end 220*b* of the sleeve 220 into a bone tunnel. As further shown in FIGS. 13 and 14, the distal end 220*b* can also be tapered to facilitate insertion into a bone tunnel. The proximal portion of the sleeve 220 can also vary in shape and size, but in an exemplary embodiment the proximal portion has a generally cylindrical shape for receiving the insert 210 therein. As further shown in FIG. 14, and as previously indicated, the sleeve 220 can also include threads 222 formed therein for mating with corresponding threads formed on the inserter shaft. While the location of the threads 222 can vary, in the illustrated embodiment the threads 222 are located just proximal to the tapered distal end 220*b* of the sleeve 220. The sleeve 220 can also include other features that will be discussed in more detail below.

Figure 15:
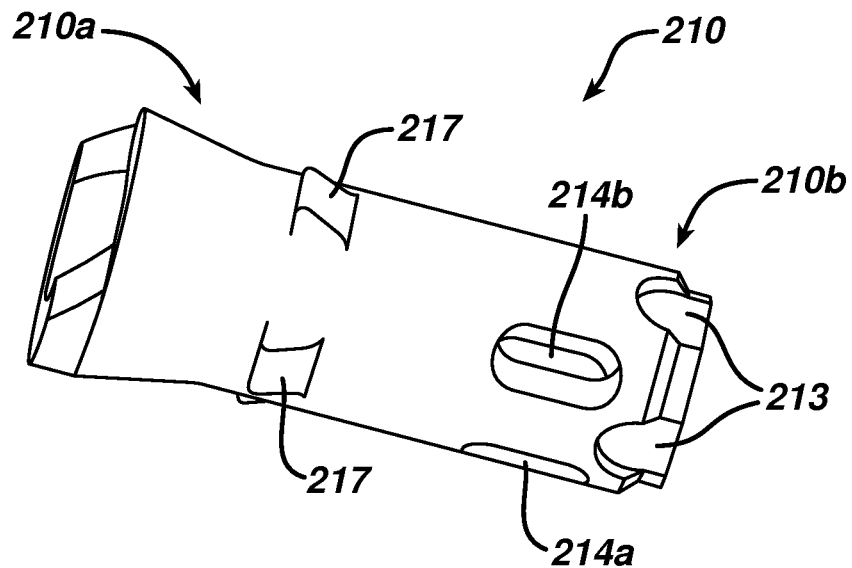
FIG. 15 is a perspective view of the insert of the suture anchor of FIG. 12.

The insert 210 is shown in more detail in FIGS. 15 and 16, and as shown the insert 210 can have a generally elongate cylindrical configuration with a distal leading end 210*b* and a proximal trailing end 210*a*. In an exemplary embodiment, at least a portion of the insert 210 has an outer diameter that is greater than an inner diameter of at least a portion of the sleeve 220 such that the insert 210 will deformably expand the sleeve 220 upon insertion of the insert 210 therein. This will allow the sleeve 220 to be embedded within the bone tunnel, thereby anchoring the suture anchor 220 in the bone tunnel. As further shown in FIG. 15, the insert 210 can also have a flared proximal end 210a that has an increased outer diameter as compared to the remainder of the insert 210. The flared proximal end 210a can be effective to expand the proximal trailing end 220a of the sleeve 220 to further facilitate engagement between the sleeve 220 and the bone tunnel within which the sleeve 220 is disposed.

As further shown in FIGS. 15 and 16, the insert 210 can also be hollow to allow the inserter shaft 110 (FIG. 10) to extend therethrough and to mate with the sleeve 220, which in this embodiment is positioned distal of the insert 210. As indicated above, the insert 210 is also preferably configured to mate to a suture for anchoring the suture to bone. While the insert 210 can include various features for mating with a suture, in the embodiment shown in FIGS. 15 and 16 the insert 210 includes first and second thru-bores 214a, 214b formed therein and configured to receive the suture therethrough. The use of two thru-bores 214a, 214b is advantageous as it allows the suture to extend into the first thru-bore 214a and out of the second thru-bore 214b such that a suture loop is formed and two trailing ends of the suture extend from the anchor 200.

As indicated above, in certain exemplary embodiments the insert 210 can be configured to deformably and optionally irreversibly expand at least a portion of the sleeve 220 into the bone tunnel. A person skilled in the art will appreciate that various materials can be used to allow the sleeve 220 to expand. In one exemplary embodiment, however, the sleeve 220 and the insert 210 can each be substantially rigid and they can have the same modulus of elasticity.

The insert 210 and the sleeve 220 can also include various other features formed thereon. For example, the insert 210 and the sleeve 220 can include an alignment mechanism formed there between and configured to radially align the insert 210 with the sleeve 220. While various alignment techniques can be used, as shown in FIGS. 13 and 14 the proximal-most end of the sleeve 220 includes a plurality of protrusions 223 extending proximally therefrom. The protrusions 223 are configured to sit within corresponding detents or bores 213 formed around a distal end of the insert 210, as shown in FIGS. 15 and 16.

In another embodiment, the insert 210 and the sleeve 220 can include an engagement mechanism formed there between for locking the insert 210 and the outer sleeve 220 together to prevent accidental removal of the insert 210 from the sleeve 2210 once the anchor 200 is implanted. While various engagement mechanisms can be used, including a friction, interference fit, mechanical interlock, etc., in one exemplary embodiment the insert 210 and the sleeve 220 include a snap-lock engagement mechanism that utilizes at least one pin and at least one complementary bore for receiving the pin. As shown in FIGS. 15 and 16, the insert 210 includes a plurality of pins 217 formed thereon and spaced around a perimeter thereof. The pins 217 increases in height in a distal to proximal direction. When the insert 210 is positioned within the sleeve 220, the pins 217 will extend into corresponding bores 227 formed in the sleeve 220 and spaced around a perimeter thereof, as shown in FIGS. 13 and 14. The increasing height of the pins 217 will allow the pins 217 to slide into the bores 227 during insertion of the insert 210 into the sleeve 220, and will allow a trailing end or distal end of each pin 217 to extend through and engage the bores 227 to prevent back-out or removal of the insert 210 from the sleeve 220. The insert 210 will thus snap-lock into the sleeve 220 to provide a secure mating connection between the two components. The aforementioned alignment mechanisms formed between the insert 210 and the pusher 120, and between the insert 210 and sleeve 220, will assist in aligning the pins 217 with the bores 227 during use.

A person skilled in the art will appreciate that the suture anchor can have a variety of other configurations, and that the suture anchor described and disclosed herein is merely one exemplary embodiment of a suture anchor for use with the present invention.

Referring back to FIG. 11, the suture anchor 200 is shown mated to the insertion assembly 100. In particular, the inserter shaft 110 extends through the insert 210 and is threadably mated to the sleeve 220 such that the distal-most tip 114 of the inserter shaft 110 extends through the opening 221 in the distal end 220b of the sleeve 220. The insert 210 is thus positioned just proximal of the sleeve 220 such that the leading distal end 210b of the insert 210 is positioned adjacent to or in contact with the trailing proximal end 220a of the sleeve 220. The protrusions on the proximal end of the sleeve 220 can seat within the detents or bores formed around the distal end of the insert 210 to radially or rotationally align the insert 210 and the sleeve 220. The proximal end 210a of the insert 210 can be positioned adjacent to or in contact with the distal end 120d of the pusher 120 such that the cut-out or notch in the proximal end of the insert 210 extends into and is aligned with the cut-out or notch in the distal end of the pusher 120. FIG. 11 also illustrates a suture threaded through the first and second thru-bores to form a suture loop on one side of the anchor. Two trailing ends 300a, 300b of the suture 300 extend proximally from the suture anchor 200.

Figure 17:
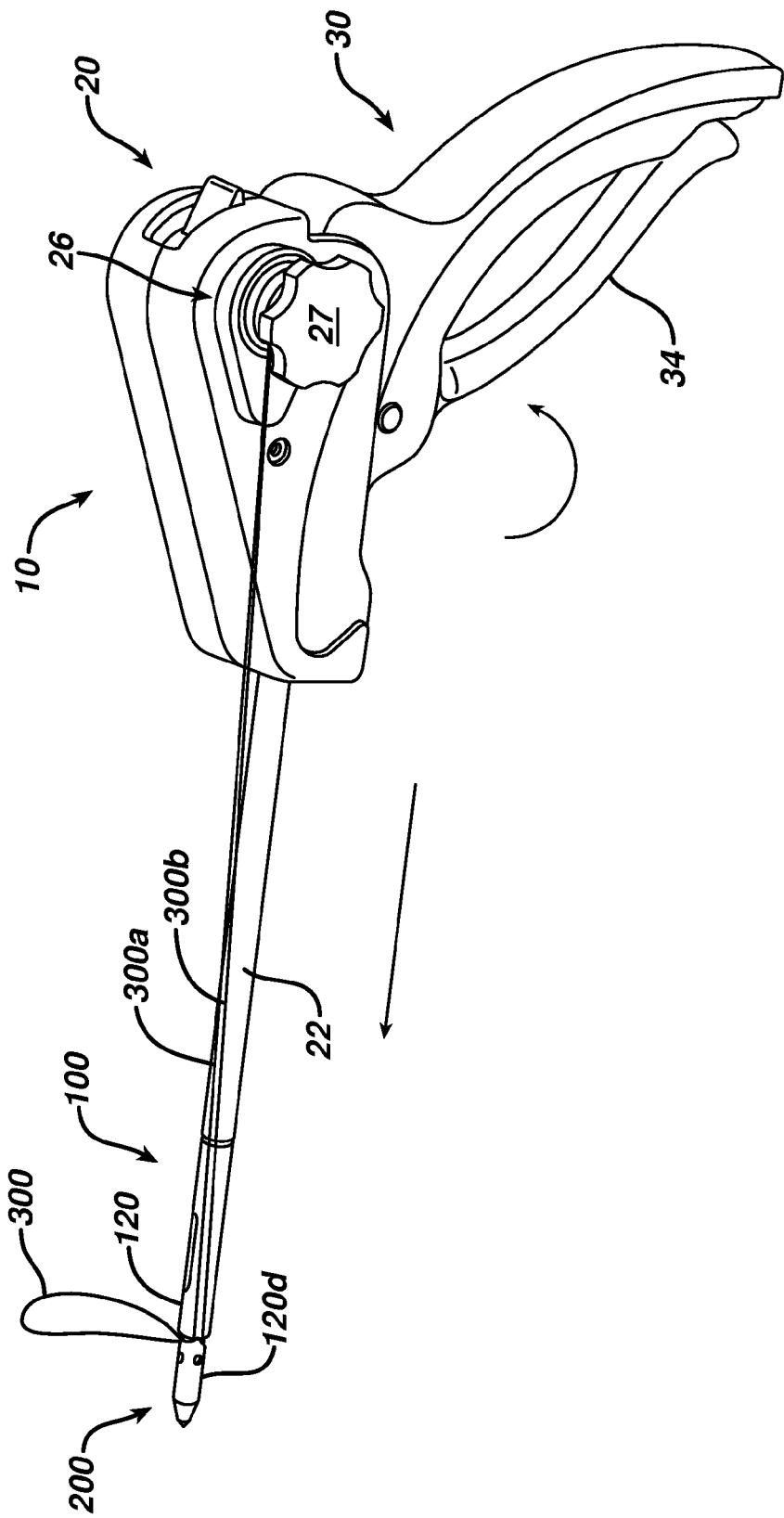
FIG. 17 is a perspective view of the suture anchor deployment device, insertion assembly, and a suture anchor of FIG. 1 having a suture coupled thereto and showing the device actuated to deploy the suture anchor.

As shown in FIG. 17 and as previously described herein, the insertion assembly 100, with the suture anchor 200 mated thereto, can be mated to a deployment device, such as device 10, for deploying the suture anchor 200 into bone. The trailing ends 300a, 300b of the suture 300 can be mated to the suture tensioning element 26 by winding the trailing ends 300a, 300b around the tensioning wheel 27, and optionally rotating the tensioning wheel 27 to increase or decrease a tension applied to the suture 300, as may be desired. The suture 300 thus remains taught between the suture anchor 200 and the suture tensioning element 26.

The suture anchor 200 can be implanted by first passing the suture through the soft tissue to be anchored, and then mating the suture to the suture anchor 200 and suture tensioning element 26. With the soft tissue mated to the suture, the inserter shaft 110 can be forced distally through into the bone, pulling the soft tissue toward the bone. It will be appreciated that, as this occurs, the suture anchor 200 will be carried into the bone in its pre-deployed configuration, due to the threaded engagement between the sleeve 220 and the inserter shaft 110. In fact, the distal end of the inserter shaft 110 and the tapered distal end of the sleeve 220 will cooperate with one another so as to force an opening in the bone, without any need for pre-drilling. The bone can, however, optionally be pre-drilled if desired, or a mallet or other device can be used to facilitate insertion into bone.

Alternatively, the suture anchor 200 can be implanted by penetrating or "stabbing" the sharp distal end of the inserter shaft 110 into soft tissue (or the like) to be anchored, and positioning it against bone to which the soft tissue is to be anchored. The trailing ends 300a, 300b of the suture 300 will remain attached to the suture tensioning element 26. The soft tissue may alternatively be gripped by another instrument (e.g., forceps or the like) and moved into position against the bone whereby the inserter shaft 110 can be forced distally through the tissue and into the bone. Again, it will be appreciated that, as this occurs, suture anchor 200 will be carried into the bone in its pre-deployed configuration, due to the threaded engagement between the sleeve 220 and the inserter shaft 110. In fact, the distal end of the inserter shaft 110 and the tapered distal end of the sleeve 220 will cooperate with one another so as to force an opening in the soft tissue and the bone, without any need for pre-drilling. As indicated above, the bone can, however, optionally be pre-drilled if desired, or a mallet or other device can be used to facilitate insertion into bone.

The inserter shaft 110 can be driven into the bone to various depths, but in an exemplary embodiment the inserter shaft 110 is driven into bone until the proximal trailing end of the insert 210 is approximately even with the outer surface of the bone. More preferably, the inserter shaft 110 can be driven deeper into bone, and the distal end 120d of the pusher 120 can act as a stop shoulder that limits the penetration depth of the inserter shaft 110. In other embodiments, markings (not shown) may be placed on the outer surface of the inserter shaft 110 so that proper depth penetration can be achieved.

Next, the trigger 34 on the deployment device 10 can be moved from the open position, shown in FIG. 1, to the closed position, shown in FIG. 17 by squeezing the trigger 34. As the trigger 34 pivots to the closed position, the handle assembly 30 will slide proximally relative to the housing 20, thus pulling the inserter shaft 110 proximally relative to the outer shaft 22. The housing 20, outer shaft 22, pusher 120, and insert 210 will remain in a substantially fixed position as the handle assembly 30, inserter shaft 110, and sleeve 220 move proximally. Thus, the suture 300 extending between the anchor 200 and the suture tensioning element 26 will remain fixed so as to not interfere with the tension applied to the suture 300. The tension thus remains unchanged. As the sleeve 220 is pulled proximally over the insert 210, the interference fit between the sleeve 220 and the insert 210 will trap and lock the suture 300 there between, and the insert 210 will be locked within the sleeve 220 using the snap-fit engagement previously discussed. The insert 210 can also cause at least a portion of the sleeve 220 to expand, e.g., the proximal portion, causing the sleeve 220 to engage the bone tunnel. Once fully deployed, the inserter shaft 110 can be unscrewed from the sleeve 220 and removed, leaving the suture anchor 200 behind. The trailing ends 300a, 300b of the suture 300 that extend from the suture anchor 200 and through the soft tissue can be knotted, e.g., using a knotting element, or otherwise fastened to secure the soft tissue to the bone.

A person skilled in the art will appreciate that the insert can optionally be advanced into the sleeve as the sleeve remains in a substantially fixed position. The tension applied to the suture in such case will still remain fixed, as the suture and tensioning element attached thereto will move with the insert. In other embodiments, the sleeve can be positioned proximal of the insert, and the insert can be retracted into the sleeve or the sleeve can be pushed over the insert.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method for deploying a suture anchor, comprising:
    inserting into a bone tunnel a suture anchor having a generally cylindrical inner component and a tubular outer component disposed coaxially with the inner component and which outer component is coupled to a distal end of a deployment device;
    coupling suture between the inner component of the suture anchor and a suture retaining element located on a housing of the deployment device; and
    actuating a handle assembly to draw the outer component of the suture anchor over the inner component of the suture anchor while maintaining the inner component in a fixed position within the bone tunnel thereby locking the suture between the inner and outer components, and wherein tension applied to the suture extending between the inner component and the housing remains substantially fixed, and expanding at least a portion of the outer component to engage the bone tunnel and lock the outer component within the bone tunnel.

2. The method of claim 1, wherein the handle assembly slides proximally relative to the housing when the handle assembly is actuated.

3. The method of claim 1, wherein actuating the handle assembly comprises pivoting a trigger coupled to the handle assembly.

4. The method of claim 1, wherein the suture retaining element comprises a suture tensioning assembly, and the method further comprises actuating the suture tensioning assembly to tension the suture between the suture tensioning assembly and the inner component of the suture anchor.

5. The method of claim 1, wherein the housing is located at a proximal end of the deployment device, and coupling the suture comprises coupling the suture between the inner component and the suture retaining member located at the proximal end of the deployment device.

6. The method of claim 1, wherein inserting the suture anchor into the bone tunnel comprises inserting the outer component of the suture anchor into the bone tunnel at a location in the bone tunnel distal to the inner component of the suture anchor.

7. The method of claim 1, wherein the outer component slides proximally relative to the housing when the handle assembly is actuated.

8. The method of claim 1, wherein the handle assembly and the outer component slidably move relative to the housing when the handle assembly is actuated.

9. The method of claim 1 wherein the inner component is held in the fixed position within the bone tunnel via an abutment adjacent the distal end of the deployment device which remains a fixed distance from the housing during the step of actuating the handle assembly.

10. The method of claim 1 wherein the inner component has a tubular outer surface and the outer component has a tubular inner surface and wherein the step of locking the suture between the inner and outer components comprises compressing the suture between the inner component outer surface and the outer component inner surface.

11. A method for deploying a suture anchor, comprising:
    inserting a suture anchor coupled to a distal end of a deployment device into a bone tunnel;
    tensioning a suture coupled to a tubular first component of the suture anchor; and
    actuating a handle assembly to slide the handle assembly relative to a housing of the deployment device, thereby mating a tubular second component of the suture anchor with the first component of the suture anchor to lock the suture between the first and second components while maintaining the position of the first component relative to the bone tunnel and maintaining substantially fixed tension in the suture, and expanding at least a portion of the second component to engage the bone tunnel.

12. The method of claim 11, wherein the second component is pulled over the first component when the handle assembly is actuated.

13. The method of claim 11, wherein tensioning the suture comprises coupling the suture between the first component of the suture anchor and a suture retaining element located on a housing of the deployment device.

14. The method of claim 13, wherein the suture retaining element, first component, and suture remain in a substantially fixed position as the handle assembly is slid relative to the housing.

15. The method of claim 13, wherein the suture retaining element comprises a suture tensioning assembly and wherein the method further comprises tensioning the suture between the first component of the suture anchor and the suture tensioning assembly.

16. The method of claim 13, wherein the suture retaining element comprises a wheel rotatably coupled to the housing, and tensioning the suture comprises rotating the wheel.

17. The method of claim 11, wherein the housing is located at a proximal end of the deployment device, and tensioning the suture comprises tensioning the suture between the first component and the housing.

18. The method of claim 11, wherein tensioning the suture comprises tensioning the suture between the first component and a proximal end of the deployment device.

19. The method of claim 11, wherein the handle assembly and the second component slide proximally relative to the housing when the handle assembly is actuated.

20. The method of claim 11, wherein the second component slidably moves relative to the housing when the handle assembly is actuated.

21. The method of claim 11, wherein inserting the suture anchor into the bone tunnel comprises inserting the second component of the suture anchor into the bone tunnel before inserting the first component of the suture anchor into the bone tunnel.

22. The method of claim 11, further comprises actuating a release mechanism coupled to the housing to release tension applied to the suture after the suture is locked between the first and second components.

* * * * *